(12) United States Patent
Chevalier et al.

(10) Patent No.: US 6,821,723 B2
(45) Date of Patent: Nov. 23, 2004

(54) GP41 ANTIGEN

(75) Inventors: Michel Chevalier, Beaurepaire (FR); Raphaëlle El Habib, Chaponost (FR); Tino Krell, Ecully (FR); Règis Sodoyer, Sainte Foy les Lyon (FR)

(73) Assignee: Aventis Pasteur S.A., Lyons Cedex (FR)

( * ) Notice: Subject to any disclaimer, the term of this patent is extended or adjusted under 35 U.S.C. 154(b) by 39 days.

(21) Appl. No.: 10/263,103

(22) Filed: Oct. 2, 2002

(65) Prior Publication Data

US 2003/0138445 A1 Jul. 24, 2003

Related U.S. Application Data

(60) Provisional application No. 60/347,909, filed on Nov. 7, 2001.

(30) Foreign Application Priority Data

Oct. 5, 2001 (FR) .............................. 01 12806

(51) Int. Cl.[7] ............................. C12Q 1/70; C12Q 1/68; C12N 5/00; A61K 39/38; A61K 39/21
(52) U.S. Cl. ............................... 435/5; 435/6; 435/325; 435/339.1; 435/320.1; 424/184.1; 424/208.1
(58) Field of Search ............................. 435/5, 6, 325, 435/339.1, 320.1; 424/184.1, 208.1

(56) References Cited

FOREIGN PATENT DOCUMENTS

| WO | WO 00 08167 | 2/2000 |
|----|-------------|--------|
| WO | WO 00 40616 | 7/2000 |
| WO | WO 01 44286 | 6/2001 |
| WO | WO 01 70262 | 9/2001 |

OTHER PUBLICATIONS

Weng, Yongkai and Weiss, Carol D., "Mutational Analysis of Residues in the Coiled–Coil Domain of Human Immunofeficiency Virus Type 1 Transmembrane Protein gp41," Journal of Virology, Dec. 1998, pp. 9676–9682.
Cao, et al., "Effects of Amino Acid Changes in the Extracellular Domain of the Human Immunodeficiency Virus Type 1 gp41 Envelope Glycoprotein," Journal of Virology, May 1993, pp. 2747–2755.
Weng, et al., "Structure–Function Studies of Self–Assembly Domain of the Human Immunodficiency Virus Type 1 Transmembrane Protein gp41," Journal of Virology, Jun. 2000, pp. 5368–5372.
LaCasse, et al., "Fusion–Competent Vaccines: Broad Neutralization of Primary Isolates of HIV," Research Articles, Jan. 15, 1999 vol. 383.
Weissenhorn, et al., "Atomic Structure of the Ectodomain from HIV–1 gp41," Nature, vol. 387, May 1999.
Malashkevich, et al., "Crystal Structure of the Simian Immunodeficiency Virus (SIV) gp41 core: Conserved Helical Interactions Underlie the Broad Inhibitory Activity of gp41 Peptides," Proc. Natl. Acad. Sci. USA vol. 95, pp. 9134–9139, Aug. 1998 Biochemistry.

(List continued on next page.)

*Primary Examiner*—Hankyel T. Park
(74) *Attorney, Agent, or Firm*—McDonnell Boehnen Hulbert & Berghoff

(57) ABSTRACT

The present invention comprises novel polypeptide antigens that can be used for therapeutic and prophylactic immunization against HIV-related infections. The polypeptide of the invention mimics the intermediate state of gp41 and is capable of inducing antibodies which neutralize primary isolates of HIV. The invention also comprises compositions comprising the polypeptide and methods of using it.

30 Claims, 4 Drawing Sheets

OTHER PUBLICATIONS

Montefiori, David C. and Evans, Thomas G., "Toward an HIV Type 1 Vaccine that Generates Potent, Broadly Cross-Reactive Neutralizing Antibodies," Aids Research and Human Retroviruses, vol. 15, No. 8, 1999, pp. 689–698.

Shu, et al., "Helical Interactions in the HIV–1 gp41 Core Reveal Structural Basis for the Inhibitory Activity of gp41 Peptides," Biochemistry 2000, 39, 1634–1642.

Louis, et al., "Design and Properties of $N_{CCG}$–gp41, a Chimeric gp41 Molecule with Nanomolar HIV Fusion Inhibitory Activity," vol. 276, No. 31, Issue of Aug. 3, pp. 29485–29489, 2001.

Wingfield, et al., "The extracellular Domain of Immunodeficiency Virus gp41 Protein: Expression in *Escherichia coli*, Purification, and Crystallization," Protein Science (1997), 6:1653–1660, Cambridge University Press.

DeRosny, et al., "Peptides Corresponding to the Heptad Repeat Motifs in the Transmembrane Protein (gp41) of Human Immunodeficiency Virus Type 1 Elicit Antibodies of Receptor–Activated Conformations of the Envelope Glycoprotein," Journal of Virology, Sep. 2001, pp. 8859–8863.

Yang, et al., "The Crystal Structure of the SIV gp41 Ectodomain at 1.47 A Resolution," Journal of Structural Biology, 126, 131–144 (1999).

Caffrey, et al., "Three–Dimensional Solution Structure of the 44 kDa Ectodomain of SIV gp41," The EMBO Journal vol. 17, No. 16, pp. 4572–4584, 1998.

Recording of the circular dichroism of the whole ectodomain of gp41 (sequence AA25-AA157, ———) and of the polypeptide SEQ ID NO : 31 in the presence (- - -) and absence (— — —) of 25 % of 2,2,2 trifluoroethanol.

SEQUENCE LISTING

```
<160> NUMBER OF SEQ ID NOS: 35
<210> SEQ ID NO 1
<211> LENGTH: 29
<212> TYPE: DNA
<213> ORGANISM: Artificial
<220> FEATURE:
<223> OTHER INFORMATION: primer

<400> SEQUENCE: 1
catgccatgg ccagacaatt attgtctgg                              29

<210> SEQ ID NO 2
<211> LENGTH: 42
<212> TYPE: DNA
<213> ORGANISM: Artificial
<220> FEATURE:
<223> OTHER INFORMATION: primer

<400> SEQUENCE: 2
```

```
ctccatccag gtcatgttat tatcctttag gtatctttcc ac            42
```

<210> SEQ ID NO 3
<211> LENGTH: 42
<212> TYPE: DNA
<213> ORGANISM: Artificial
<220> FEATURE:
<223> OTHER INFORMATION: primer

<400> SEQUENCE: 3

```
gtggaaagat acctaaagga taataacatg acctggatgg ag            42
```

<210> SEQ ID NO 4
<211> LENGTH: 66
<212> TYPE: DNA
<213> ORGANISM: Artificial
<220> FEATURE:
<223> OTHER INFORMATION: primer

<400> SEQUENCE: 4

```
ccgctcgagc taatggtgat ggtgatggtg tgaccctccc cctcctttat ctaattccaa    60
taattc                                                              66
```

<210> SEQ ID NO 5
<211> LENGTH: 29
<212> TYPE: DNA
<213> ORGANISM: Artificial
<220> FEATURE:
<223> OTHER INFORMATION: primer

<400> SEQUENCE: 5

```
catgccatgg ccagacaatt attgtctgg                           29
```

<210> SEQ ID NO 6
<211> LENGTH: 47
<212> TYPE: DNA
<213> ORGANISM: Artificial
<220> FEATURE:
<223> OTHER INFORMATION: primer

<400> SEQUENCE: 6

```
gttaatttct ctgtcccact ccatccactg ttgatccttt aggtatc       47
```

<210> SEQ ID NO 7
<211> LENGTH: 47
<212> TYPE: DNA
<213> ORGANISM: Artificial
<220> FEATURE:
<223> OTHER INFORMATION: primer

<400> SEQUENCE: 7

```
gatacctaaa ggatcaacag tggatggagt gggacagaga aattaac       47
```

<210> SEQ ID NO 8
<211> LENGTH: 66
<212> TYPE: DNA
<213> ORGANISM: Artificial
<220> FEATURE:
<223> OTHER INFORMATION: primer

<400> SEQUENCE: 8

```
ccgctcgagc taatggtgat ggtgatggtg tgaccctccc cctcctttat ctaattccaa    60
taattc                                                              66
```

```
<210> SEQ ID NO 9
<211> LENGTH: 29
<212> TYPE: DNA
<213> ORGANISM: Artificial
<220> FEATURE:
<223> OTHER INFORMATION: primer

<400> SEQUENCE: 9
catgccatgg ccagacaatt attgtctgg                              29

<210> SEQ ID NO 10
<211> LENGTH: 36
<212> TYPE: DNA
<213> ORGANISM: Artificial
<220> FEATURE:
<223> OTHER INFORMATION: primer

<400> SEQUENCE: 10
catccaggtc atgttattat cctttaggta tctttc                      36

<210> SEQ ID NO 11
<211> LENGTH: 36
<212> TYPE: DNA
<213> ORGANISM: Artificial
<220> FEATURE:
<223> OTHER INFORMATION: primer

<400> SEQUENCE: 11
gaaagatacc taaaggataa taacatgacc tggatg                      36

<210> SEQ ID NO 12
<211> LENGTH: 65
<212> TYPE: DNA
<213> ORGANISM: Artificial
<220> FEATURE:
<223> OTHER INFORMATION: primer

<400> SEQUENCE: 12
ccgctcgagc taatggtgat ggtgatggtg tgaccctccc cctcctttat ctaattccaa    60
taatt                                                               65

<210> SEQ ID NO 13
<211> LENGTH: 36
<212> TYPE: DNA
<213> ORGANISM: Artificial
<220> FEATURE:
<223> OTHER INFORMATION: primer

<400> SEQUENCE: 13
ttattggaat tagataaagc cagacaatta ttgtct                      36

<210> SEQ ID NO 14
<211> LENGTH: 63
<212> TYPE: DNA
<213> ORGANISM: Artificial
<220> FEATURE:
<223> OTHER INFORMATION: primer

<400> SEQUENCE: 14
ccgctcgagc taatggtgat ggtgatggtg tgaccctccc cctcccttta ggtatctttc    60
cac                                                                 63

<210> SEQ ID NO 15
<211> LENGTH: 31
<212> TYPE: DNA
```

-continued

<210> SEQ ID NO 15
<211> LENGTH: 31
<212> TYPE: DNA
<213> ORGANISM: Artificial
<220> FEATURE:
<223> OTHER INFORMATION: primer

<400> SEQUENCE: 15
catgccatgg gatggatgga gtgggacaga g                            31

<210> SEQ ID NO 16
<211> LENGTH: 36
<212> TYPE: DNA
<213> ORGANISM: Artificial
<220> FEATURE:
<223> OTHER INFORMATION: primer

<400> SEQUENCE: 16
agacaataat tgtctggctt tatctaattc caataa                       36

<210> SEQ ID NO 17
<211> LENGTH: 39
<212> TYPE: DNA
<213> ORGANISM: Artificial
<220> FEATURE:
<223> OTHER INFORMATION: primer

<400> SEQUENCE: 17
ggaattagat aaatgggcag ccagacaatt attgtctgg                    39

<210> SEQ ID NO 18
<211> LENGTH: 63
<212> TYPE: DNA
<213> ORGANISM: Artificial
<220> FEATURE:
<223> OTHER INFORMATION: primer

<400> SEQUENCE: 18
ccgctcgagc taatggtgat ggtgatggtg tgaccctccc cctcccttta ggtatctttc    60
cac                                                                 63

<210> SEQ ID NO 19
<211> LENGTH: 31
<212> TYPE: DNA
<213> ORGANISM: Artificial
<220> FEATURE:
<223> OTHER INFORMATION: primer

<400> SEQUENCE: 19
catgccatgg gatggatgga gtgggacaga g                            31

<210> SEQ ID NO 20
<211> LENGTH: 39
<212> TYPE: DNA
<213> ORGANISM: Artificial
<220> FEATURE:
<223> OTHER INFORMATION: primer

<400> SEQUENCE: 20
ccagacaata attgtctggc tgcccattta tctaattcc                    39

<210> SEQ ID NO 21
<211> LENGTH: 40
<212> TYPE: DNA
<213> ORGANISM: Artificial
<220> FEATURE:
<223> OTHER INFORMATION: primer

<400> SEQUENCE: 21

```
gggcaagttt gtggaattgg gccagacaat tattgtctgg                             40
```

<210> SEQ ID NO 22
<211> LENGTH: 63
<212> TYPE: DNA
<213> ORGANISM: Artificial
<220> FEATURE:
<223> OTHER INFORMATION: primer

<400> SEQUENCE: 22

```
ccgctcgagc taatggtgat ggtgatggtg tgaccctccc cctcccttta ggtatctttc      60
cac                                                                   63
```

<210> SEQ ID NO 23
<211> LENGTH: 31
<212> TYPE: DNA
<213> ORGANISM: Artificial
<220> FEATURE:
<223> OTHER INFORMATION: primer

<400> SEQUENCE: 23

```
catgccatgg gatggatgga gtgggacaga g                                     31
```

<210> SEQ ID NO 24
<211> LENGTH: 40
<212> TYPE: DNA
<213> ORGANISM: Artificial
<220> FEATURE:
<223> OTHER INFORMATION: primer

<400> SEQUENCE: 24

```
ccagacaata attgtctggc ccaattccac aaacttgccc                            40
```

<210> SEQ ID NO 25
<211> LENGTH: 200
<212> TYPE: PRT
<213> ORGANISM: Artificial
<220> FEATURE:
<223> OTHER INFORMATION: polypeptide

<400> SEQUENCE: 25

```
Ala Val Gly Ile Gly Ala Leu Phe Leu Gly Phe Leu Gly Ala Ala Gly
1               5                   10                  15

Ser Thr Met Gly Ala Ala Ser Met Thr Leu Thr Val Gln Ala Arg Gln
            20                  25                  30

Leu Leu Ser Gly Ile Val Gln Gln Gln Asn Asn Leu Leu Arg Ala Ile
        35                  40                  45

Glu Ala Gln Gln His Leu Leu Gln Leu Thr Val Trp Gly Ile Lys Gln
    50                  55                  60

Leu Gln Ala Arg Ile Leu Ala Val Glu Arg Tyr Leu Lys Asp Gln Gln
65                  70                  75                  80

Leu Leu Gly Ile Trp Gly Cys Ser Gly Lys Leu Ile Cys Thr Thr Ala
                85                  90                  95

Val Pro Trp Asn Ala Ser Trp Ser Asn Lys Ser Leu Glu Gln Ile Trp
            100                 105                 110

Asn Asn Met Thr Trp Met Glu Trp Asp Arg Glu Ile Asn Asn Tyr Thr
        115                 120                 125

Ser Leu Ile His Ser Leu Ile Glu Glu Ser Gln Asn Gln Gln Glu Lys
    130                 135                 140

Asn Glu Gln Glu Leu Leu Glu Leu Asp Lys Trp Ala Ser Leu Trp Asn
```

```
                145                 150                 155                 160
Trp Phe Asn Ile Thr Asn Trp Leu Trp Tyr Ile Lys Asn Arg Val Arg
                    165                 170                 175

Gln Gly Tyr Ser Pro Leu Ser Phe Gln Thr His Leu Pro Thr Pro Arg
                180                 185                 190

Gly Pro Asp Arg Pro Glu Gly Ile
        195                 200
```

<210> SEQ ID NO 26
<211> LENGTH: 48
<212> TYPE: PRT
<213> ORGANISM: Artificial
<220> FEATURE:
<223> OTHER INFORMATION: polypeptide

<400> SEQUENCE: 26

```
Ala Arg Gln Leu Leu Ser Gly Ile Val Gln Gln Gln Asn Asn Leu Leu
1               5                   10                  15

Arg Ala Ile Glu Ala Gln Gln His Leu Leu Gln Leu Thr Val Trp Gly
                20                  25                  30

Ile Lys Gln Leu Gln Ala Arg Ile Leu Ala Val Glu Arg Tyr Leu Lys
            35                  40                  45
```

<210> SEQ ID NO 27
<211> LENGTH: 38
<212> TYPE: PRT
<213> ORGANISM: Artificial
<220> FEATURE:
<223> OTHER INFORMATION: polypeptide

<400> SEQUENCE: 27

```
Trp Met Glu Trp Asp Arg Glu Ile Asn Asn Tyr Thr Ser Leu Ile His
1               5                   10                  15

Ser Leu Ile Glu Glu Ser Gln Asn Gln Gln Glu Lys Asn Glu Gln Glu
                20                  25                  30

Leu Leu Glu Leu Asp Lys
        35
```

<210> SEQ ID NO 28
<211> LENGTH: 105
<212> TYPE: PRT
<213> ORGANISM: Artificial
<220> FEATURE:
<223> OTHER INFORMATION: polypeptide

<400> SEQUENCE: 28

```
Met Ala Arg Gln Leu Leu Ser Gly Ile Val Gln Gln Gln Asn Asn Leu
1               5                   10                  15

Leu Arg Ala Ile Glu Ala Gln Gln His Leu Leu Gln Leu Thr Val Trp
                20                  25                  30

Gly Ile Lys Gln Leu Gln Ala Arg Ile Leu Ala Val Glu Arg Tyr Leu
            35                  40                  45

Lys Asp Asn Asn Met Thr Trp Met Glu Trp Asp Arg Glu Ile Asn Asn
        50                  55                  60

Tyr Thr Ser Leu Ile His Ser Leu Ile Glu Glu Ser Gln Asn Gln Gln
65                  70                  75                  80

Glu Lys Asn Glu Gln Glu Leu Leu Glu Leu Asp Lys Gly Gly Gly Gly
                85                  90                  95

Ser His His His His His Leu Glu
            100                 105
```

<210> SEQ ID NO 29
<211> LENGTH: 103
<212> TYPE: PRT
<213> ORGANISM: Artificial
<220> FEATURE:
<223> OTHER INFORMATION: polypeptide

<400> SEQUENCE: 29

Met Ala Arg Gln Leu Leu Ser Gly Ile Val Gln Gln Gln Asn Asn Leu
1               5                   10                  15

Leu Arg Ala Ile Glu Ala Gln Gln His Leu Leu Gln Leu Thr Val Trp
            20                  25                  30

Gly Ile Lys Gln Leu Gln Ala Arg Ile Leu Ala Val Glu Arg Tyr Leu
        35                  40                  45

Lys Asp Gln Gln Trp Met Glu Trp Asp Arg Glu Ile Asn Asn Tyr Thr
    50                  55                  60

Ser Leu Ile His Ser Leu Ile Glu Glu Ser Gln Asn Gln Gln Glu Lys
65                  70                  75                  80

Asn Glu Gln Glu Leu Leu Glu Leu Asp Lys Gly Gly Gly Gly Ser His
                85                  90                  95

His His His His His Leu Glu
            100

<210> SEQ ID NO 30
<211> LENGTH: 105
<212> TYPE: PRT
<213> ORGANISM: Artificial
<220> FEATURE:
<223> OTHER INFORMATION: polypeptide

<400> SEQUENCE: 30

Met Ala Arg Gln Leu Leu Ser Gly Ile Val Gln Gln Gln Asn Asn Leu
1               5                   10                  15

Leu Arg Ala Ile Glu Ala Gln Gln His Leu Leu Gln Leu Thr Val Trp
            20                  25                  30

Gly Ile Lys Gln Leu Gln Ala Arg Ile Leu Ala Val Glu Arg Tyr Leu
        35                  40                  45

Lys Asp Asn Asn Met Thr Trp Met Glu Trp Asp Arg Glu Ile Asn Asn
    50                  55                  60

Tyr Thr Ser Leu Ile His Ser Leu Ile Glu Glu Ser Gln Asn Gln Gln
65                  70                  75                  80

Glu Lys Asn Glu Gln Glu Leu Leu Glu Leu Asp Lys Gly Gly Gly Gly
                85                  90                  95

Ser His His His His His Leu Glu
            100                 105

<210> SEQ ID NO 31
<211> LENGTH: 101
<212> TYPE: PRT
<213> ORGANISM: Artificial
<220> FEATURE:
<223> OTHER INFORMATION: polypeptide

<400> SEQUENCE: 31

Met Gly Trp Met Glu Trp Asp Arg Glu Ile Asn Asn Tyr Thr Ser Leu
1               5                   10                  15
Ile His Ser Leu Ile Glu Glu Ser Gln Asn Gln Gln Lys Asn Glu
            20                  25                  30
Gln Glu Leu Leu Glu Leu Asp Lys Ala Arg Gln Leu Leu Ser Gly Ile
        35                  40                  45

```
Val Gln Gln Gln Asn Asn Leu Leu Arg Ala Ile Glu Ala Gln Gln His
    50                  55                  60
Leu Leu Gln Leu Thr Val Trp Gly Ile Lys Gln Leu Gln Ala Arg Ile
65                  70                  75                  80
Leu Ala Val Glu Arg Tyr Leu Lys Gly Gly Gly Gly Ser His His His
                85                  90                  95
His His His Leu Glu
            100

SEQ ID NO 32
LENGTH: 103
TYPE: PRT
ORGANISM: Artificial
FEATURE:
OTHER INFORMATION: polypeptide

SEQUENCE: 32

Met Gly Trp Met Glu Trp Asp Arg Glu Ile Asn Asn Tyr Thr Ser Leu
1               5                   10                  15

Ile His Ser Leu Ile Glu Glu Ser Gln Asn Gln Gln Glu Lys Asn Glu
                20                  25                  30

Gln Glu Leu Leu Glu Leu Asp Lys Trp Ala Ala Arg Gln Leu Leu Ser
            35                  40                  45

Gly Ile Val Gln Gln Gln Asn Asn Leu Leu Arg Ala Ile Glu Ala Gln
        50                  55                  60

Gln His Leu Leu Gln Leu Thr Val Trp Gly Ile Lys Gln Leu Gln Ala
65                  70                  75                  80

Arg Ile Leu Ala Val Glu Arg Tyr Leu Lys Gly Gly Gly Gly Ser His
                85                  90                  95

His His His His His Leu Glu
            100

<210> SEQ ID NO 33
<211> LENGTH: 108
<212> TYPE: PRT
<213> ORGANISM: Artificial
<220> FEATURE:
<223> OTHER INFORMATION: polypeptide

<400> SEQUENCE: 33

Met Gly Trp Met Glu Trp Asp Arg Glu Ile Asn Asn Tyr Thr Ser Leu
1               5                   10                  15

Ile His Ser Leu Ile Glu Glu Ser Gln Asn Gln Gln Glu Lys Asn Glu
                20                  25                  30

Gln Glu Leu Leu Glu Leu Asp Lys Trp Ala Ser Leu Trp Asn Trp Ala
            35                  40                  45

Arg Gln Leu Leu Ser Gly Ile Val Gln Gln Gln Asn Asn Leu Leu Arg
        50                  55                  60

Ala Ile Glu Ala Gln Gln His Leu Leu Gln Leu Thr Val Trp Gly Ile
65                  70                  75                  80

Lys Gln Leu Gln Ala Arg Ile Leu Ala Val Glu Arg Tyr Leu Lys Gly
                85                  90                  95

Gly Gly Ser His His His His His His Leu Glu
            100                 105

<210> SEQ ID NO 34
<211> LENGTH: 552
<212> TYPE: DNA
<213> ORGANISM: Artificial
<220> FEATURE:
<223> OTHER INFORMATION: gp41 core region
```

```
<400> SEQUENCE: 34
atgacgctga cggtacaggc cagacaatta ttgtctggta tagtgcagca gcagaacaat    60
ttgctgaggg ctattgaggc gcaacagcat ctgttgcaac tcacagtctg gggcatcaag   120
cagctccagg caagaatcct ggctgtggaa agatacctaa aggatcaaca gctcctgggg   180
atttggggtt gctctggaaa actcatttgc accactgctg tgccttggaa tgctagttgg   240
agtaataaat ctctggaaca gatttggaat aacatgacct ggatggagtg ggacagagaa   300
attaacaatt acacaagctt aatacattcc ttaattgaag aatcgcaaaa ccagcaagaa   360
aagaatgaac aagaattatt ggaattagat aaatgggcaa gtttgtggaa ttggtttaac   420
ataacaaatt ggctgtggta tataaaaaat agagttaggc agggatattc accattatcg   480
tttcagaccc acctcccaac cccgagggga cccgacaggc ccgaaggagg tagagagcga   540
gtccgagacc ga                                                       552

<210> SEQ ID NO 35
<211> LENGTH: 5312
<212> TYPE: DNA
<213> ORGANISM: Artificial
<220> FEATURE:
<223> OTHER INFORMATION: plasmid pET-cer

<400> SEQUENCE: 35
tggcgaatgc cttaattaag gcggggcaca actcaatttg cgggtactga ttaccgcagc    60
aaagacctta ccccgaaaaa atccaggctg ctggctgaca cgatttctgc ggtttatctc   120
gatggctacg agggcagaca gtaagtggat ttaccataat cccttaattg tacgcaccgc   180
taaaacgcgt tcagcgcgat cacgcagca gacaggtaaa aatggcaaca accacccga   240 aaaactgccg cgatcgcgcc tgataaattt taaccgtatg aatacctatg caaccagagg   300
gtacaggcca cattaccccc acttaatcca ctgaagctgc cattttttcat ggtttcacca   360 tcccagcgaa gggccatcca gcgtgcgttc ctgtatttcc gactggcgcg ccattcaggt   420 ggcactttc ggggaaatgt gcgcggaacc cctatttgtt tattttttcta atacattca   480 aatatgtatc cgctcatgaa ttaattctta gaaaaactca tcgagcatca aatgaaactg   540
caatttattc atatcaggat tatcaatacc atatttttga aaaagccgtt tctgtaatga   600
aggagaaaac tcaccgaggc agttccatag gatggcaaga tcctggtatc ggtctgcgat   660
tccgactcgt ccaacatcaa tacaacctat taatttcccc tcgtcaaaaa taaggttatc   720
aagtgagaaa tcaccatgag tgacgactga atccggtgag aatggcaaaa gtttatgcat   780
ttctttccag acttgttcaa caggccagcc attacgctcg tcatcaaaat cactcgcatc   840
aaccaaaccg ttattcattc gtgattgcgc ctgagcgaga cgaaatacgc gatcgctgtt   900
aaaaggacaa ttacaaacag gaatcgaatg caaccggcgc aggaacactg ccagcgcatc   960
aacaatattt tcacctgaat caggatattc ttctaatacc tggaatgctg ttttcccggg  1020
gatcgcagtg gtgagtaacc atgcatcatc aggagtacgg ataaaatgct tgatggtcgg  1080
aagaggcata aattccgtca gccagtttag tctgaccatc tcatctgtaa catcattggc  1140
aacgctacct ttgccatgtt tcagaaacaa ctctggcgca tcgggcttcc catacaatcg  1200
atagattgtc gcacctgatt gcccgacatt atcgcgagcc catttatacc catataaatc  1260
agcatccatg ttggaattta atcgcggcct agagcaagac gtttcccgtt gaatatggct  1320
cataacaccc cttgtattac tgtttatgta agcagacagt tttattgttc atgaccaaaa  1380
tcccttaacg tgagttttcg ttccactgag cgtcagaccc cgtagaaaag atcaaaggat  1440
```

-continued

```
cttcttgaga tcctttttt ctgcgcgtaa tctgctgctt gcaaacaaaa aaaccaccgc      1500
taccagcggt ggtttgtttg ccggatcaag agctaccaac tcttttccg aaggtaactg       1560
gcttcagcag agcgcagata ccaaatactg tccttctagt gtagccgtag ttaggccacc      1620
acttcaagaa ctctgtagca ccgcctacat acctcgctct gctaatcctg ttaccagtgg      1680
ctgctgccag tggcgataag tcgtgtctta ccgggttgga ctcaagacga tagttaccgg      1740
ataaggcgca gcggtcgggc tgaacggggg gttcgtgcac acagcccagc ttggagcgaa      1800
cgacctacac cgaactgaga tacctacagc gtgagctatg agaaagcgcc acgcttcccg      1860
aagggagaaa ggcggacagg tatccggtaa gcggcagggt cggaacagga gagcgcacga     1920
gggagcttcc aggggggaaac gcctggtatc tttatagtcc tgtcgggttt cgccacctct    1980
gacttgagcg tcgattttg tgatgctcgt caggggggcg gagcctatgg aaaaacgcca      2040
gcaacgcggc cttttacgg ttcctggcct tttgctggcc ttttgctcac atgttctttc      2100
ctgcgttatc ccctgattct gtgggtaacc gtattaccgc ctttgagtga gctgataccg     2160
ctcgccgcag ccgaacgacc gagcgcagcg agtcagtgag cgaggaagcg gaagagcgcc    2220
tgatgcggta ttttctcctt acgcatctgt gcggtatttc acaccgcaat ggtgcactct    2280
cagtacaatc tgctctgatg ccgcatagtt aagccagtat acactccgct atcgctacgt    2340
gactgggtca tggctgcgcc ccgacacccg ccaacacccg ctgacgcgcc ctgacgggct   2400
tgtctgctcc cggcatccgc ttacagacaa gctgtgaccg tctccgggag ctgcatgtgt    2460
cagaggttt caccgtcatc accgaaacgc gcgaggcagc tgcggtaaag ctcatcagcg    2520
tggtcgtgaa gcgattcaca gatgtctgcc tgttcatccg cgtccagctc gttgagtttc    2580
tccagaagcg ttaatgtctg gcttctgata aagcgggcca tgttaagggc ggttttttcc   2640
tgtttggtca ctgatgcctc cgtgtaaggg ggatttctgt tcatgggggt aatgataccg   2700
atgaaacgag agaggatgct cacgatacgg gttactgatg atgaacatgc ccggttactg    2760
gaacgttgtg agggtaaaca actggcggta tggatgcggc gggaccagag aaaaatcact   2820
cagggtcaat gccagcgctt cgttaataca gatgtaggtg ttccacaggg tagccagcag   2880
catcctgcga tgcagatccg gaacataatg gtgcagggcg ctgacttccg cgtttccaga   2940
ctttacgaaa cacggaaacc gaagaccatt catgttgttg ctcaggtcgc agacgttttg    3000
cagcagcagt cgcttcacgt tcgctcgcgt atcggtgatt cattctgcta accagtaagg    3060
caaccccgcc agcctagccg ggtcctcaac gacaggagca cgatcatgcg cacccgtggg   3120
gccgccatgc cggcgataat ggcctgcttc tcgccgaaac gtttggtggc gggaccagtg    3180
acgaaggctt gagcgagggc gtgcaagatt ccgaataccg caagcgacag gccgatcatc    3240
gtcgcgctcc agcgaaagcg gtcctcgccg aaaatgaccc agagcgctgc cggcacctgt    3300
cctacgagtt gcatgataaa gaagacagtc ataagtgcgg cgacgatagt catgccccgc    3360
gcccaccgga aggagctgac tgggttgaag gctctcaagg gcatcggtcg agatcccggt    3420
gcctaatgag tgagctaact tacattaatt gcgttgcgct cactgcccgc tttccagtcg    3480
ggaaacctgt cgtgccagct gcattaatga atcggccaac gcgcggggag aggcggtttg    3540
cgtattgggc gccagggtgg ttttctttt caccagtgag acgggcaaca gctgattgcc     3600
cttcaccgcc tggccctgag agagttgcag caagcggtcc acgctggttt gccccagcag    3660
gcgaaaatcc tgtttgatgg tggttaacgg cgggatataa catgagctgt cttcggtatc    3720
gtcgtatccc actaccgaga tatccgcacc aacgcgcagc ccggactcgg taatggcgcg    3780
```

-continued

```
cattgcgccc agcgccatct gatcgttggc aaccagcatc gcagtgggaa cgatgccctc    3840
attcagcatt tgcatggttt gttgaaaacc ggacatggca ctccagtcgc cttcccgttc    3900
cgctatcggc tgaatttgat tgcgagtgag atatttatgc cagccagcca gacgcagacg    3960
cgccgagaca gaacttaatg ggcccgctaa cagcgcgatt tgctggtgac ccaatgcgac    4020
cagatgctcc acgcccagtc gcgtaccgtc ttcatgggag aaaataatac tgttgatggg    4080
tgtctggtca gagacatcaa gaaataacgc cggaacatta gtgcaggcag cttccacagc    4140
aatggcatcc tggtcatcca gcggatagtt aatgatcagc ccactgacgc gttgcgcgag    4200
aagattgtgc accgccgctt tacaggcttc gacgccgctt cgttctacca tcgacaccac    4260
cacgctggca cccagttgat cggcgcgaga tttaatcgcc gcgacaattt gcgacggcgc    4320
gtgcagggcc agactggagg tggcaacgcc aatcagcaac gactgtttgc ccgccagttg    4380
ttgtgccacg cggttgggaa tgtaattcag ctccgccatc gccgcttcca cttttcccg    4440 cgttttcgca gaaacgtggc tggcctggtt caccacgcgg gaaacggtct gataagagac    4500
accggcatac tctgcgacat cgtataacgt tactggtttc acattcacca ccctgaattg    4560
actctcttcc gggcgctatc atgccatacc gcgaaaggtt ttgcgccatt cgatggtgtc    4620
cgggatctcg acgctctccc ttatgcgact cctgcattag gaagcagccc agtagtaggt    4680
tgaggccgtt gagcaccgcc gccgcaagga atggtgcatg caaggagatg gcgcccaaca    4740
gtcccccggc cacggggcct gccaccatac ccacgccgaa acaagcgctc atgagcccga    4800 agtgcgagc ccgatcttcc ccatcggtga tgtcggcgat ataggcgcca gcaaccgcac    4860
ctgtggcgcc ggtgatgccg gccacgatgc gtccggcgta gaggatcgag atctcgatcc    4920
cgcgaaatta atacgactca ctatagggga attgtgagcg gataacaatt cccctctaga    4980
aataattttg tttaacttta agaaggagat ataccatggg cagcagccat catcatcatc    5040
atcacagcag cggcctggtg ccgcgcggca gccatatggc tagcatgact ggtggacagc    5100
aaatgggtcg gatccgaatt cgagctccgt cgacaagctt gcggccgcac tcgagcacca    5160
ccaccaccac cactgagatc cggctgctaa caaagcccga aaggaagctg agttggctgc    5220
tgccaccgct gagcaataac tagcataacc ccttggggcc tctaaacggg tcttgagggg    5280
ttttttgctg aaaggaggaa ctatatccgg at                                  5312
```

GP41 ANTIGEN

This application claims the benefit of U.S. Provisional Patent Application No. 60/347,909 filed on Nov. 7, 2001.

The present invention relates to a polypeptide antigen which derives from the gp41 protein, and also to its use for immunization against HIV-related infections; these studies were cofinanced by the ANRS [French National Association for AIDS Research].

The development of a method of immunization against HIV is, to lay, one of the priorities of scientific research.

The major obstacles represented by the great genetic variability of the virus and the low exposure to the immune system of neutralizing viral epitopes considerably hinder the development of neutralizing immunity.

The HIV envelope glycoprotein, which is required to confer on the virus its infectious nature, represents the target for neutralizing antibodies. These characteristics have made this glycoprotein a subject of intense investigation.

The envelope glycoprotein (env) of the human immunodeficiency virus-1 (HIV-1) is synthesized from the precursor gp160, which gives, under the action of a protease, the gp120 and gp41 subunits.

The attachment of gp120/gp41 to the cellular receptors induces a change in conformation of gp41, from a latent (nonfusogenic) state to an active-fusion (fusogenic) state. Between these two states, there exists a transient "intermediate" state, during which gp41 is like a membrane-bound protein which is in both the viral and cell membranes (Weissenhorn et al. Nature (1997), 387 (6631), 426–30).

The use of gp41 in its fusogenic conformation, for immunization purposes, is described in WO 00/40616. According to that application, the N-helices can be used alone or in combination with the C-helices so as to reproduce, in the latter case, the fusogenic conformation of gp41.

Binding experiments have made it possible to establish, firstly, that the nonfusogenic latent state is characterized by the inaccessibility of large portions of the ectodomain of gp41. gp120 in fact interacts so as to mask the epitopes. It has, moreover, been shown that inhibition of the change in structure of the intermediate state to the fusogenic state with peptides used as competitors may affect viral infection (Weissenhorn W. et al., Molecular Membrane Biology, 1999, 16, 3–9).

The applicant proposes a novel polypeptide antigen which can be used for therapeutic and prophylactic immunization against HIV-related infections. The applicant has, in fact, demonstrated, for the first time, that a polypeptide which mimics the intermediate state of gp41 is capable of inducing antibodies which neutralize primary isolates of HIV.

The present invention therefore relates to a polypeptide comprising a sequence of formula I:

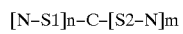

[N–S1]n–C–[S2–N]m in which:

N represents the sequence of amino acids 30 to 77 of gp41,

C represents the sequence of amino acids 117 to 154 of gp41,

S1 and S2 are, independently of one another, either absent or represent an amino acid sequence such that the sequence of formula I adopts an alpha-helical conformation as determined by the SOPMA program under the following conditions:

number of conformational states=4
similarity limit=8, and
window width=70
n=0 or 1; m=0 or 1 and m+n=1 or 2.

Preferably, the polypeptide as defined above comprises a sequence of formula I in which m+n=1.

Preferably, S1 is absent or represents the amino acid sequence D, DQ, DQQ, DQQL or DNNMT, and S2 is absent or represents the amino acid sequence W, WA, WAS, WASL or WASLW.

The S1 and S2 amino acid sequences are defined using the one letter code in which D represents aspartic acid, Q represents glutamine, etc.

According to a particular embodiment, the polypeptide comprises a sequence of formula I as defined above, in which N represents SEQ ID No. 26 and C represents SEQ ID No. 27.

According to a preferred embodiment, the polypeptide is selected in the group consisting of SEQ ID No. 28 and SEQ ID No. 31.

According to another embodiment, the polypeptide according to the invention comprises an additional sequence of formula (G)a-S—(H)b in which G represents a glycine residue, H represents a histidine residue S is a serine, a is greater than or equal to 4 and b is greater than or equal to 6. Said sequence is linked via an amide bond to the NH$_2$-terminal end or COOH-terminal end of the polypeptide according to the invention.

According to another aspect, the present invention relates to a conjugate comprising a polypeptide according to the invention conjugated to a carrier protein or peptide.

According to another aspect, the present invention relates to a DNA sequence encoding a polypeptide according to the invention or a conjugate according to the invention.

The present invention also relates to an expression vector comprising said DNA sequence, and also to a host cell containing said vector.

A subject of the present invention is also a pharmaceutical composition comprising at least one polypeptide as defined above, at least one conjugate as defined above or at least one expression vector as defined above, a pharmaceutically acceptable excipient and, optionally, an adjuvant.

According to a particular embodiment, the present invention relates to a pharmaceutical composition as defined above which can be administered orally.

A subject of the present invention is therefore also the polypeptide as defined above, for its use as a medicinal product, and in particular for its use in immunizing the human body against HIV-related infections.

Another subject of the present invention relates to the method for preparing a polypeptide as described above, comprising the expression of said polypeptide using a host cell as defined above.

The invention is described in greater detail in the description which follows.

The phenomenon of conformational change of gp41 which precedes the cell and viral membrane fusion is illustrated in FIG. 1. Attachment of gp120 to the receptor and the coreceptor of the virus causes a first modification which leads to unfolding of the fusion peptide and anchoring thereof in the cell membrane. At this time, an intermediate state forms, in which there is no interaction between the N-helices and the C-helices. The second event illustrated in FIG. 1 is the folding of gp41, which corresponds to the molecule adopting a thermodynamically more stable conformation. The energy released during this folding allows the lipids of the cell and viral membranes to come close to one another and fuse.

The Applicant has demonstrated, surprisingly, that the polypeptide according to the invention induces specific IgG antibodies which neutralize HIV primary isolates. The induction of antibodies which neutralize primary isolates can be determined using the neutralization test as described in the article by C. Moog et al. (AIDS Research and human retroviruses, Vol. 13(1), 13–27, 1997), to which reference may be made for a complete description of the latter. In the context of the present invention, it is estimated that neutralizing antibodies have been induced by the antigen tested according to the technique of C. Moog when the serum diluted at least to ¼, in the presence of HIV, leads to a 10-fold decrease in the viral titer in comparison to HIV alone, the viral titer being evaluated by the amount of p24 produced in the culture supernatant.

The induction of antibodies which neutralize primary isolates may also be determined using the neutralization test of D. Montefiori as described in J. Infect. Dis. 1996, 173:60–67. In this test, the neutralizing titer is expressed by the percentage decrease in p24 antigen produced in the culture supernatants when the virus is incubated in the presence of serum diluted to ¼, by comparison with the virus in the absence of serum. In the context of the present invention, it is considered that neutralizing antibodies have been induced when the decrease in the level of p24 produced reaches at least 80% with a serum diluted to ¼.

In the context of the present invention, it is considered that the antibodies induced by the polypeptide according to the invention are neutralizing antibodies if neutralizing activity is detected for a given isolate in at least one of the two tests above.

The induction of antibodies which neutralize the HIV-1 MN laboratory strain can be estimated using the MT-2 cell line according to the method of D. Montefiori, described in: DC Montefiori et al., J. Clin. Microbiol. 1988, 26: 231–5). In this method, the neutralizing titer is expressed as the inverse of the dilution of the serum (in arithmetic value) which protects at least 50% of cells against the cytopathogenic effect of the HIV virus.

This property makes the polypeptide according to the invention an immunization candidate of interest for humans.

The polypeptide according to the present invention has the particularity of adopting, under physiological conditions, a conformation which may be termed "open", as opposed to the "closed" conformation of gp41 in fusogenic form in which the N and C domains are paired with one another according to an anti-parallel orientation (cf. FIG. 1).

Specifically, the open conformation of the polypeptide according to the invention is characterized in that the C sequence is not paired with the N sequence according to the anti-parallel orientation as present in the fusogenic form. The polypeptide according to the present invention is preferably in a trimeric form in which the N sequences and the C sequences are, respectively, paired with one another according to a parallel orientation.

The applicant has also demonstrated, surprisingly, that the polypeptide according to the invention conserves its "open" conformation in highly acid medium. This property makes the polypeptide according to the invention an immunization antigen which can be administered orally. The applicant has, in fact, shown that the ectodomain of the gp41 protein is extremely thermostable at pH 2.5.

Measurement of the Tm (temperature at which 50% of the proteins present are denatured) of gp41 in 50 mM sodium formate by DSC (differential scanning calorimetry) gives a value of 110° C., the beginning of the denaturation phenomenon appearing at approximately 100° C. at pH=2.5. The thermostability of the gp41 protein at neutral pH has been evaluated by Weissenhorn et al. (EMBO, 1996, 7, 1507–1514). The Tm measured at neutral pH by these authors is 78° C., which means that, surprisingly, this protein is more stable at acid pH than at neutral pH. These results have been confirmed by circular dichroism analysis aimed at calculating the percentage of alpha-helix in the protein.

The applicant has also shown that the polypeptide according to the invention has the same particularity. This specific property makes the polypeptide according to the invention an immunization antigen of choice for oral administration.

This open conformation is obtained by the direct attachment of the N and C sequences as defined above. In such a case, S1 and S2 are absent and the last amino acid of the N sequence is directly linked, via an amide bond, to the first amino acid of the C sequence, or inversely (example: AA33-77-AA117-154). This open conformation is also obtained when the N and C sequences as defined above are connected to one another via an S1 or S2 sequence such that the resulting sequence of formula I adopts an alpha-helical conformation as determined by the SOPMA program under the following conditions: number of conformational states=4; similarity limit=8 and window width=70.

The open conformation according to the invention is, in fact, characterized by the absence of a flexible region between the N and C sequences. The SOPMA program available on the site: http://npsa-pbil.ibcp.fr/cgi-bin/npsa__automat.pl?page=/NPSA/npsa__sopma.html (Geourjon C and Deléage G. SOPMA, Casios (1995), 11, 681–684) makes it possible to easily determine whether the S1 or S2 sequence adopts, in the context of the polypeptide of formula I, an alpha-helical conformation which is suitable in the context of the present invention.

According to a preferred embodiment, m+n=1 and, if S1 is absent, S2 represents W, WA, WAS, WASL or WASLW and, if S2 is absent, S1 represents D, DQ, DQQ, DQQL or DNNMT.

In addition, according to a particularly preferred embodiment, in the polypeptide as defined above, the sequences AA30-AA77 and AA117-AA154 correspond, respectively, to the sequences SEQ ID No. 26 and SEQ ID No. 27.

According to a preferred embodiment, the polypeptide is selected in the group consisting of SEQ ID No. 28 and SEQ ID No. 31.

The sequences AA30-AA77 and AA117-AA154 derived from gp41 are numbered by taking, as a reference, the numbering of the sequence of the gp41 protein as given in the sequence listing under the title SEQ ID No. 25. The sequence SEQ ID No. 25 corresponds to a truncated gp41 LAI protein in which the first amino acid A bears the number 1.

The sequences AA30-AA77 and AA 117-AA154 according to the present invention may be derived from any gp41 protein of HIV, including the HIV1 and HIV2 strains, including the laboratory strains and primary isolates. Preferably, the N and C sequences according to the present invention are derived from an HIV1 strain, and in particular from an HIV1 LAI strain.

The nucleotide and peptide sequences of a large number of gp41 proteins are known and available, for example, on the Internet on the site http://hiv-web.lanl.gov/, and also in the corresponding Los Alamos compendia. It is clear that any sequence into which one or more conservative mutations which do not substantially modify either the immunogenicity or the open conformation have been introduced is also included in the context of the present invention.

The open conformation according to the present invention is characterized by a certain number of parameters which can be measured by the DSC technique and the circular dichroism technique. These techniques are described in detail in the following articles by A. Cooper et al., Phil Trans. R. Soc. Lon. A (1993) 345, 23–25, and by V. V. Plotnikov et al. Analytical Biochemistry 250, 237–244, (1997) and S. M. Kelly and N. C. Price (1997) Biochim. Biophys. Acta. 1338, 161–185.

DSC measures the thermodynamic parameters of protein denaturation. Protein denaturation is an endothermic event which can be evaluated by measuring the absorption of heat by the protein as a function of temperature. The two main parameters obtained are:

the Tm or half-denaturation point (i.e. temperature at which 50% of the protein is present in native form and 50% in denatured form) and the $\Delta H$ or variation in enthalpy during denaturation (i.e. the heat required to denature the protein).

These two parameters are precise markers of the conformation of a protein. A DSC analysis is detailed in example 5 with reference to FIG. 2.

As regards the circular dichroism technique, it makes it possible to evaluate the secondary structure of the protein. The signal for an alpha-helix is characterized by minima at 208 nm and 222 nm. The value of the signal at 222 nm is used to determine the percentage of alpha-helix in a protein. The signal for a loop is characterized by a maximum at approximately 205 nm. This technique makes it possible to demonstrate that the polypeptide according to the invention does not contain the loop normally present in the fusogenic form and that it consists almost exclusively, or even exclusively, of an alpha-helix.

A circular dichroism analysis is detailed in example 6 with reference to FIG. 3.

Although the polypeptide according to the invention has an open conformation which is stable, this conformation may be reinforced by adding cysteine residues to the ends of the polypeptide. To this end, two additional cysteine residues may be added at the N-terminal or at the C-terminal, preferably at the N-terminal, of the polypeptide according to the invention so as to covalently fix the trimer in an open conformation.

The polypeptide according to the invention may be obtained using any conventional technique of chemical synthesis or of genetic engineering.

When the polypeptide is produced by chemical synthesis, the polypeptide according to the invention may be synthesized in the form of a single sequence, or in the form of several sequences which are then linked to one another. The chemical synthesis may be carried out in solid phase or in solution, these two synthesis techniques being well known to those skilled in the art. These techniques are described in particular by Atherton and Shepard in "solid phase peptide synthesis (IRL press Oxford, 1989) and by Houbenweyl in "method der organischen chemie" edited by E. Wunsch vol, 15-I and II thieme, Stuttgart, 1974, and also in the following articles, which are entirely incorporated herein by way of reference: Dawson P E et al. (Synthesis of proteins by native chemical ligation Science 1994; 266(5186):776–9); Kochendoerfer G G et al. (Chemical protein synthesis Curr Opin Chem Biol 1999; 3(6):665–71); and Dawson P E et al. Synthesis of native proteins by chemical ligation, Annu rev Biochem 2000; 69:923–60.

The polypeptide according to the invention may also be produced using genetic engineering techniques which are well known to those skilled in the art. When the polypeptide according to the invention is produced by genetic engineering, it comprises an additional $NH_2$-terminal methionine residue corresponding to the translation of the first initiation codon and it may further comprises additional N-and/or C-terminal amino-acid(s). These techniques are described in detail in Molecular Cloning: a molecular manual by Maniatis et al., Cold Spring Harbor, 1989). Conventionally, the DNA sequence encoding the polypeptide according to the invention may be produced by the PCR technique, in which the N and C sequences are, firstly, amplified independently of one another and are then, secondly, paired and again amplified. The DNA sequence thus obtained is then inserted into an expression vector. The expression vector containing the sequence of interest is then used to transform a host cell which allows the expression of the sequence of interest. The polypeptide produced is then isolated from the culture medium using conventional techniques well known to those skilled in the art, such as ethanol precipitation or ammonium sulfate precipitation, acid extraction, anion/cation exchange chromatography, phosphocellulose chromatography, hydrophobic interaction chromatography, affinity chromatography, hydroxyapatite chromatography or lectin chromatography. Preferably, high performance liquid chromatography (HPLC) is used in the purification.

Depending on the expression system used (secreted or nonsecreted protein) and depending on the purification method, the purified polypeptide may be in various forms. It may be in a denatured or nondenatured, monomeric or multimeric form. When it is in a denatured form, it is possible to turn it to its open conformation according to the invention using the method described in the examples given hereinafter. To obtain multimeric forms, and in particular trimers, the purified polypeptide molecules must be placed in a medium which allows the molecules to be completely soluble and to have essentially no interaction with one another and preferably no secondary structure. For this, it is possible to use detergents such as sodium dodecyl sulfate, N-lauryl sarcosine, guanidinium chloride, urea, sodium thiocyanate or chaotropic agents. The desired conditions may be promoted by using organic solvents or using acids. Once this first condition is satisfied, the sample is placed in a dialysis cassette in order to remove part of the detergents or of the chaotropic agents used, so as to promote the interactions between the polypeptide monomers while conserving sufficient solubility for the molecules. In a second step, once the formation of trimers has been promoted, the sample is completely dialyzed in a physiological medium which keeps the polypeptide in solution or in suspension. Trimers of the polypeptide according to the invention are thus obtained. Such a technique is described in detail in WO 00/08167.

To carry out the synthesis of the polypeptide, any expression vector conventionally used for expressing a recombinant protein may be used in the context of the present invention. This term therefore encompasses both "live" expression vectors, such as viruses and bacteria, and expression vectors of the plasmid type.

Vectors in which the DNA sequence of the polypeptide according to the invention is under the control of a strong promoter, which may be inducible or noninducible, are preferably used. By way of example of a promoter which may be used, mention may be made of the T7 RNA polymerase promoter.

The expression vectors preferably include at least one selection marker. Such markers include, for example, the dihydrofolate reductase gene or the neomycin resistance gene, for culturing eukaryotic cells, and the kanamycin resistance, tetracycline resistance or ampicillin resistance genes, for culturing in *E. coli* and other bacteria.

By way of an expression vector which may be used in the context of the present invention, mention may be made of the pET28 (Novagen) or pBAD (Invitrogen) plasmids for example, viral vectors such as: baculoviruses, poxviruses, in particular the poxviruses described in patents U.S. Pat. Nos. 5,942,235, 5,756,103 and 5,990,091, which are entirely incorporated herein by way of reference, and recombinant vaccinia viruses, in particular the recombinant viruses described in patents EP 83286, U.S. Pat. Nos. 5,494,807 and 5,762,938, in which the DNA sequence encoding a polypeptide according to the invention is cloned.

To promote the expression and the purification of the polypeptide, the latter may be expressed in a modified form, such as a fusion protein, and may include not only secretion signals, but also additional heterologous functional regions. For example, a region of additional amino acids, particularly charged amino acids, may be added to the N-terminal of the polypeptide to improve stability and persistence in the host cell.

For expression of the polypeptide, any host cell conventionally used in combination with the expression vectors described above may be used.

By way of nonlimiting example, mention may be made of the *E. coli* cells BL21 (λDE3), HB101, Top 10, CAG 1139, *Bacillus*, and eukaryotic cells such as CHO or Vero.

In the context of the present invention, use will preferably be made of the following expression vector/cell system: pET(Cer)/BL21LambdaDE3 or BL21-lambdaDE3(RIL).

Depending on the host cell used for expressing the polypeptide, the polypeptides of the present invention may be glycosylated or nonglycosylated. In addition, the polypeptides according to the invention may also include an additional N-terminal methionine residue as well as some additional N- or C-terminal amino acid residues resulting from the recombination process.

Once purified, the polypeptide according to the invention may advantageously be mixed with 2,2,2-trifluoroethanol (TFE). To do this, the polypeptide is preferably placed in an acid buffer, such as sodium formate at pH=2.5. The mixture thus formed contains from 10 to 50% by volume of TFE, preferably from 15 to 30% by volume of TFE. The effect of the TFE is to increase the degree of helicity of the polypeptide so as to take it to a value close or equal to 100%.

Besides the TFE, other organic solvents or detergents may also be used. By way of example, mention may be made of: isopropanol or lysophospholipid. The suitable amounts of these compounds may be easily determined by those skilled in the art. Since these compounds are in general toxic and, consequently, cannot be administered to humans, it is necessary to eliminate them before administration. The applicant has demonstrated that these solvents or detergents may be easily eliminated by adding a support which adsorbs the polypeptide. The support used in the context of the present invention corresponds to a pharmaceutically acceptable support which may be administered to humans. By way of example of a support which may be used in the context of the present invention, mention may be made of the aluminum hydroxide, phosphate or hydroxyphosphate gels which are conventionally used as adjuvants in vaccines. The support is used in large excess compared to the polypeptide so as to obtain total adsorption of the latter.

Any other pharmaceutically acceptable support capable of adsorbing the polypeptide according to the invention may be used in the context of the present invention.

Conventionally, the required amount of pharmaceutically acceptable support is added to the polypeptide/TFE mixture and the entire mixture is then incubated at room temperature for the amount of time necessary to allow total absorption of the polypeptide onto the support. The incubation period may vary from 15 min to 3 h. The mixture is then centrifuged once or twice at approximately 10 000 g and the pellet is taken up in a solution which can be administered to humans, such as for example in the case of an injectable composition of the PBS buffer or a physiological saline solution.

A subject of the present invention is also the conjugates comprising a polypeptide according to the invention and a carrier protein or a carrier peptide.

The carrier protein (or peptide) strengthens the immunogenicity of the polypeptide according to the invention, in particular by increasing the production of specific antibodies. Said carrier protein (or peptide) preferably comprises one or more T helper epitope(s). The term "T helper epitope" is intended to mean a chain of amino acids which, in the context of one or more class II MHC molecules, activates T helper lymphocytes. According to an advantageous embodiment, the carrier protein (or peptide) used improves the water-solubility of the polypeptide according to the invention.

As carrier protein, use may be made, for example, of phage surface proteins, such as the pIII or pVIII protein of the M13 phage, bacterial surface proteins, such as the LamB, OmpC, ompA, ompF and PhoE proteins of *E. coli*, the CotC or CotD protein of *B. subtilis*, bacterial porins, such as *Neisseria gonorrheae* porin P1, *H. influenzae* B porin P1 or P2, *N. meningitidis* B class I porin or *K. pneumoniae* porin P40, lipoproteins, such as *B. bugdorfi* OspA, *S. pneumoniae* PspA, *N. meningitidis* B TBP2, *E. coli* TraT and also *S. pneumoniae* adhesin A, and the heat shock proteins, such as Hsp65 or Hsp71 of *M. tuberculosis* or bovis, or Hin 47 of *H. influenzae* type B. Detoxified bacterial toxins, such as the tetanus or diphtheria toxoid, the cholera toxin B subunit, the B subunit of *P. aeruginosa* endotoxin A or *S. aureus* exotoxin A.

In the context of the present invention, as a carrier peptide, use may be made, for example, of the p24E, p24N, p24H and p24M peptides described in WO 94/29339 and also the PADRE peptides as described by Del guercio et al. (Vaccine (1997); vol 15/4, p 441–448).

The carrier protein (or peptide) is linked to the N- or C-terminal end of the polypeptide according to the invention using any conjugation method well known to those skilled in the art. In addition, the sequence encoding the carrier protein (or peptide) may advantageously be fused to the sequence encoding the polypeptide according to the invention, and the resulting sequence may be expressed in the form of a fusion protein using any conventional method. All the genetic engineering techniques which are useful for doing this are described in Maniatis et al. Said conjugates may be isolated using any conventional purification method well known to those skilled in the art.

A subject of the present invention is also the DNA sequences encoding the polypeptides and the conjugates according to the invention, and also the expression vectors comprising said sequences and the host cells transformed with said sequences. The DNA sequences encoding the polypeptides according to the invention may be easily produced by PCR using, as a matrix, the nucleotide sequence of a gp41 protein.

Rather than extracting and purifying the polypeptide or the conjugate expressed by the expression vector, it is often easier and sometimes more advantageous to use the expression vector itself in the vaccine according to the invention. A subject of the present invention is therefore any expression vector as defined above. In such a situation, the expression vector lacks a marker and preferably corresponds to a viral vector, in particular a poxvirus such as ALVAC or NYVAC.

Any host cell as defined above transformed with an expression vector is also included in the context of the present invention.

A subject of the present invention is also the antibodies directed against the polypeptides and conjugates as described above. The preparation of such antibodies is carried out using conventional techniques for producing polyclonal and monoclonal antibodies, well known to those skilled in the art.

These antibodies are particularly suitable for use in a passive immunization scheme.

A subject of the present invention is also pharmaceutical compositions which are of use for inducing HIV neutralizing antibodies which are useful for the purposes of therapeutic and prophylactic immunization against HIV-related infections. The compositions according to the present invention comprise at least one polypeptide, at least one conjugate or at least one expression vector as defined above, a pharmaceutically acceptable diluent or excipient and, optionally, an adjuvant.

According to a preferred embodiment, the composition according to the invention also comprises a pharmaceutically acceptable support. Any pharmaceutically acceptable support capable of adsorbing the polypeptide according to the invention may be used. A description of such supports has been provided above. When the pharmaceutically acceptable support is an aluminum salt, the latter performs both the function of support and that of adjuvant.

The amount of polypeptide, of conjugate or of vector in the composition according to the present invention depends on many parameters, as will be understood by those skilled in the art, such as the nature of the carrier protein, the vector used or the route of administration. A suitable amount is an amount such that a humoral immune response capable of neutralizing primary isolates of HIV is induced after administration of this amount. The amount of polypeptide to be administered is of the order of 10 $\mu$g to 1 mg, the amount selected varying depending on the route of administration. The amount of conjugate to be administered will be deduced from the amounts indicated above, taking into account the MW of the carrier protein. The amount of expression vector to be administered is of the order of 10 to 5000 micrograms in the case of a nonviral vector, and of the order of $10^E4$ to $10^E8$ TCID50 in the case of a viral vector.

The pharmaceutical compositions according to the present invention may also contain an adjuvant. Any pharmaceutically acceptable adjuvant or mixture of adjuvants conventionally used in the field of vaccines may be used for this purpose. By way of example, mention may be made of aluminum salts, such as aluminum hydroxide or aluminum phosphate. Conventional auxiliary agents, such as wetting agents, fillers, emulsifiers, buffers, etc., may also be added to the composition according to the invention.

The compositions according to the present invention may be prepared using any conventional method known to those skilled in the art. Conventionally, the antigens according to the invention are mixed with a pharmaceutically acceptable diluent or excipient, such as water or phosphate buffered saline solution. The excipient or diluent will be selected as a function of the pharmaceutical form chosen, of the method and route of administration, and also of pharmaceutical practice. Suitable excipients or diluents, and also the requirements in terms of pharmaceutical formulation, are described in detail in Remington's Pharmaceutical Sciences, which represents a reference work in this field.

The compositions mentioned above may be administered via any conventional route usually used in the field of vaccines, such as the parenteral (intravenous, intramuscular, subcutaneous, etc.) route. In the context of the present invention, intramuscular administration will preferably be used for the injectable compositions. Such an administration may advantageously take place in the thigh or arm muscles. The compositions according to the present invention may also advantageously be administered orally. Administration via the nasal, vaginal or rectal mucosa may also be recommended in the context of the present invention. The administration may also be carried out by giving a single dose or repeated doses, for example on D0 and at 1 month, 3 months, 6 months and 12 months. Injections at J0 and at 1 month and 3 months, with a booster, the periodicity of which may easily be determined by the treating physician, will preferably be used.

The pharmaceutical composition according to the present invention may advantageously be administered according to a dosage scheme comprising the co-administration of an expression vector according to the invention and of a polypeptide according to the invention, or according to a "prime-boost" scheme in which the vector according to the invention is administered first and the polypeptide is administered as a booster injection. In these two dosage schemes, the expression vector according to the invention may be replaced with any expression vector comprising furthermore one or more HIV antigens or epitopes other than the polypeptide according to the invention, and in particular with a poxvirus, preferably ALVAC or NYVAC. By way of examples of ALVAC and NYVAC vectors which can be used for this purpose, mention may be made of the vectors described in patents U.S. Pat. Nos. 5,942,235, 5,756,103 and 5,990,091; EP 83286, U.S. Pat. Nos. 5,494,807 and 5,762,938. In the context of the compositions which can be administered orally, bacterial vectors such as lactobacillus or salmonella may also advantageously be used. The use of these bacterial vectors for immunization purposes is described in detail in International Journal of Food Microbiology 41 (1998) 155–167 by P. H. Pouwels et al. and Cell vol 91, 765–775, Dec, 1997 by A. Darji et al., to which reference may be made for greater detail.

The present invention is also intended to cover a polypeptide, a conjugate or a vector as defined above, and the pharmaceutical composition containing these compounds, for their use as a medicinal product, in particular for inducing HIV neutralizing antibodies useful for prophylactic and therapeutic immunization of the human body against HIV-related infections.

According to a preferred aspect, a subject of the present invention is the use of a polypeptide according to the invention for immunizing the human body. The present invention therefore preferably relates to a method for administering said polypeptide so as to induce a specific humoral response.

The present invention thus provides a method for inducing HIV neutralizing antibodies comprising administration of a quantity of a pharmaceutical composition as defined above which is sufficient to induce the said humoral response.

According to a preferred embodiment, the method comprises the administration of a composition comprising SEQ ID No. 28 or SEQ ID No. 31.

The expression "a specific humoral response" is intended to mean a response comprising the production of antibodies directed specifically against the polypeptide according to the invention. The production of specific antibodies may be easily determined using conventional techniques well known to those skilled in the art, such as ELISA, RIA or western blot.

The applicant has demonstrated, surprisingly, that the polypeptide according to the invention is capable, after administration, of inducing antibodies capable of neutralizing primary isolates of HIV. These antigens therefore represent candidates of value for developing a vaccine which can be used for the protection and/or treatment of a large number, or even all, of the individuals at risk from or infected with HIV.

Without wishing to be bound by any theory, the applicant thinks that the "open" conformation of the polypeptide according to the invention makes accessible gp41 domains which are accessible, during the phenomenon of viral and cell membrane fusion, only in the intermediate conformation which is transiently adopted. These domains made accessible would constitute the target of the antibodies induced by the polypeptide according to the invention, these antibodies thus blocking the membrane fusion phenomenon at a prefusogenic stage. The open conformation adopted by the polypeptide according to the invention is therefore thought to mimic the conformation adopted by the intermediate state.

A subject of the invention is also a diagnostic method comprising bringing a polypeptide according to the invention into contact with a biological sample and detecting the antibody/polypeptide complexes which are formed. HIV+ individuals have, in fact, anti-gp41 serum antibodies. An immunoassay (such as an ELISA assay in which the polypeptide according to the invention is attached to the assay plate and then brought into contact with the serum to be tested, and the antibody/polypeptide complexes are then detected) would therefore make it possible to diagnose infected individuals.

The Present Invention Will be Described in Greater Detail in the Examples which Follow, with Reference to the Attached Figures in which.

Figure 4:
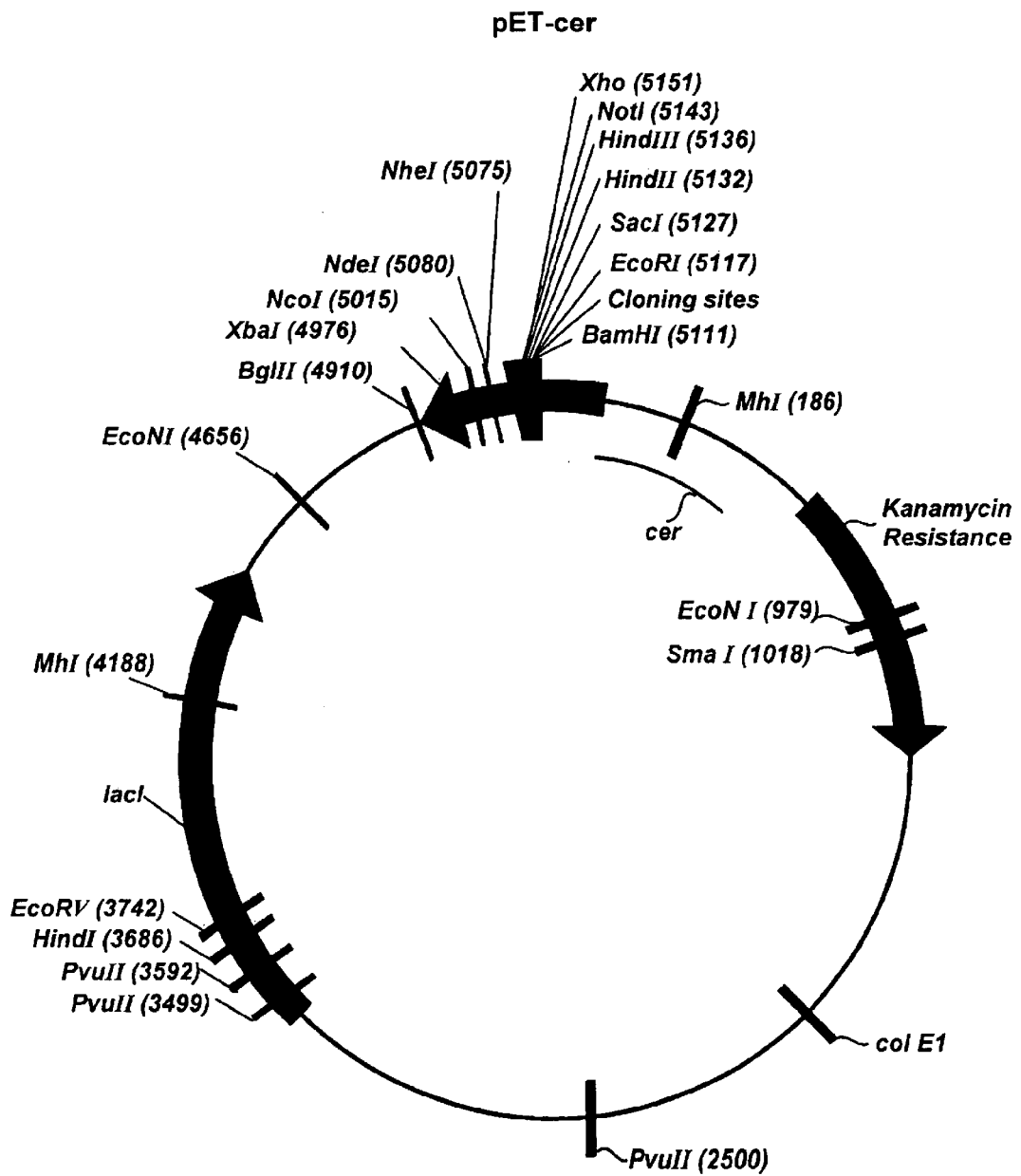

FIG. 4 gives the plasmid map of pET-Cer (SEQ ID No. 35).

The examples described below are given purely by way of illustration of the invention and can in no way be considered to limit the scope of the latter.

EXAMPLE 1
Construction of the DNA Sequences Encoding the Polypeptides According to the Invention The DNA sequences encoding the polypeptides corresponding to the sequences SEQ ID No. 28, 29, 30, 31, 32 and 33 were obtained by PCR according to the following method:

The N and C sequences are, firstly, amplified by PCR from a matrix corresponding to a plasmid containing the DNA sequence encoding the core region of gp41 (SEQ ID No. 34), using the pairs of primers 5'N/3'N and 5'C/3'C as defined below in table 1. For each of the sequences, the PCR reaction is carried out under the following conditions:

Firstly, the primers, the matrix, the nucleotide mixture and the Taq polymerase are mixed and the mixture is brought to 94° C. for 2 minutes. The resulting mixture is then subjected to 25 PCR cycles according to the following scheme: 94° 30s, 55° 30s, and 68° 30s. The products thus amplified are then purified on QIAQUICK columns under the conditions recommended by the manufacturer.

The two products thus purified, which comprise overlapping sequences, are mixed and subjected to a PCR amplification reaction using the 5'N and 3'C primers as defined below in table 1. The PCR reaction is carried out according to the following scheme: the purified N and C sequences, the Taq polymerase and the nucleotide mixture are mixed and subjected to 10 cycles: 94° 30s, 55° 30s, and 68° 30s. The 5'N and 3'C primers are then added and the resulting mixture is subjected to 20 PCR cycles according to the following scheme: 94° 30s, 55° 30s, and 68° 30s.

The DNA sequences thus amplified are then purified on QIAQUICK columns under the conditions recommended by the manufacturer.

TABLE 1

Primers used in the PCR amplification reactions

Construction of SEQ ID No 28

```
5'N CAT GCC ATG GCC AGA CAA TTA TTG TCT GG
3'N CTC CAT CCA GGT CAT GTT ATT ATC CTT TAG GTA TCT TTC CAC
5'C GTG GAA AGA TAC CTA AAG GAT AAT AAC ATG ACC TGG ATG GAG
3'C CCG CTC GAG CTA ATG GTG ATG GTG ATG GTG TGA CCC TCC CCC TCC TTT ATC TAA TTC CAA TAA TTC
```

Construction of SEQ ID No 29

```
5'N CAT GCC ATG GCC AGA CAA TTA TTG TCT GG
3'N GTT AAT TTC TCT GTC CCA CTC CAT CCA CTG TTG ATC CTT TAG GTA TC
5'C GAT ACC TAA AGG ATC AAC AGT GGA TGG AGT GGG ACA GAG AAA TTA AC
3'C CCG CTC GAG CTA ATG GTG ATG GTG ATG GTG TGA CCC TCC CCC TCC TTT ATC TAA TTC CAA TAA TTC
```

Construction of SEQ ID No 30

```
5'N CAT GCC ATG GCC AGA CAA TTA TTG TCT GG
3'N CAT CCA GGT CAT GTT ATT ATC CTT TAG GTA TCT TTC
5'C GAA AGA TAC CTA AAG GAT AAT AAC ATG ACC TGG ATG
3'C CCG CTC GAG CTA ATG GTG ATG GTG ATG GTG TGA CCC TCC CCC TCC TTT ATC TAA TTC CAA TAA TTC
```

TABLE 1-continued

Primers used in the PCR amplification reactions

Construction of SEQ ID No 31

5'N TTA TTG GAA TTA GAT AAA GCC AGA CAA TTA TTG TCT
3'N CCG CTC GAG CTA ATG GTG ATG GTG ATG GTG TGA CCC TCC CCC TCC CTT TAG GTA TCT TTC CAC
5'C CAT GCC ATG GGA TGG ATG GAG TGG GAC AGA G
3'C AGA CAA TAA TTG TCT GGC TTT ATC TAA TTC AAA TAA

Construction of SEQ ID No 32

5'N GGA ATT AGA TAA ATG GGC AGC CAG ACA ATT ATT GTC TGG
3'N CCG CTC GAG CTA ATG GTG ATG GTG ATG GTG TGA CCC TCC CCC TCC CTT TAG GTA TCT TTC CAC
5'C CAT GCC ATG GGA TGGATG GAG TGG GAC AGA G
3'C CCA GAC AAT AAT TGT CTG GCT GCC CAT TTA TCT AAT TCC

Construction of SEQ ID No 33

5'N GGG CAA GTT TGT GGA ATT GGG CCA GAC AAT TAT TGT CTG GCCG CTC GAG
3'N CTA ATG GTG ATG GTG ATG GTG TGA CCC TCC CCCTCC CTT TAG GTA TCT TTC CAC
5'C CAT GCC ATG GGA TGG ATG GAG TGG GAC AGA GCCA GAC AAT AAT TGT CTG
3'C GCC CAA TTC CAC AAA CTT GCC C

EXAMPLE 2
Cloning the DNA Sequences of Example 1 into an Expression Vector

The DNA sequences produced in example 1 are digested with NcoI and XhoI under standard conditions using 10 units of each enzyme per µg of PCR fragment, and then cloned into a vector pET-cer according to the following procedure: the PCR fragment and the vector digested with the NcoI and XhoI enzymes are ligated to one another and then used to transform an XL1 bacterial strain by electroporation. The production of the construct is verified by minipreparation of the plasmid and sequencing.

The pET-cer vector used is constructed from the vector pET28 from Novagen. The commercial vector pET28c was amplified via PCR using 2 primers located on either side of the region corresponding to the origin f1, such that the amplified product corresponds to virtually the entire vector of origin minus the region comprising the origin f1. The unique restriction sites AscI and PacI are introduced, respectively, via the 2 primers which were used for the amplification. In parallel, the cer fragment is amplified using 2 primers which make it possible to obtain this fragment bordered by the AscI and PacI sites.

The vector and cer fragment are digested with the AscI and PacI enzymes and then ligated to one another.

This vector comprises in particular an expression cassette under the control of the T7 promoter, a polylinker downstream of the T7 promoter for cloning the gene of interest, the cer fragment located downstream of the polylinker, making it possible to decrease plasmid multimerization, a transcription terminator T7 term and the kanamycin resistance gene.

Positive regulation of the promoter is obtained in the presence of T7 RNA polymerase.

The plasmid map of the pET-cer plasmid is given in FIG. 4 (SEQ ID No. 35).

EXAMPLE 3
Preparation of the Polypeptide SEQ ID No. 31 According to the Invention 1-Expression The plasmid derived from example 2, containing the sequence encoding the polypeptide SEQ ID No. 31, is expressed in a modified strain of E. coli, i.e. BL21 RILλDE3.

This strain is enriched in rare tRNAs (ARG, ILE, LEU); it contains the gene encoding T7 RNA polymerase, which is under the control of the lac UV5 promoter which can be induced by adding IPTG at a concentration of 1 mM.

Firstly, the strain is transformed with the plasmid according to the protocol comprising the following steps: 3 colonies are subcultured in 10 ml of LB supplemented with kanamycin at a concentration of 25 µg/µl; overnight incubation at 37° C.; the preculture is reseeded at 1:100 in 15 ml of LB supplemented with kanamycin at a concentration of 25 µg/µl; it is left to grow until an OD600 of 0.5 is reached; 1 ml is taken to verify the OD600; 7 ml are taken for the noninduced sample; the other 7 ml are induced with 1 mM of IPTG and induction occurs for 3 h at 37° C.

The same protocol was carried out on several liters of culture in order to produce a large amount of bacteria to purify the polypeptide according to the invention.

2-Purification

The cell pellet, made up of the bacteria harvested from 500 ml of culture medium, is thawed and taken up in 100 ml of 50 mM Tris-HCl buffer at pH 8.0 in the presence of a protease inhibitor (Pefabloc, Interchim) at the concentration of 100 µM. Lysozyme is added at the concentration of 100 µg/ml and the mixture is incubated for 30 minutes at room temperature with stirring. The cells are then ruptured by sonication (4 cycles of two minutes) with an approximate power of 150 Watts. Benzonase (DNase, Merck) is then added along with 1 mM MgCl$_2$ and the mixture is incubated for 20 min at room temperature with stirring. After centrifugation (20 min at 10 000 g), the polypeptide according to the invention is in the insoluble fraction in the form of inclusion bodies. The latter are washed with 50 mM Tris-HCl buffer at pH 8.0 and centrifuged for 15 min at 10 000 g.

The polypeptide according to the invention may then be purified using one of the following two methods:

Method 1: After elimination of the supernatant, the centrifugation pellet, composed essentially of inclusion bodies, is solubilized in one hour at room temperature by gentle stirring in the presence of 50 ml of CAPS buffer at pH 11.0 containing 1% of N-lauryl sarcosine.

The solubilized fraction is then dialyzed at 4° C. against 50 mM Tris-HCl buffer at pH 8.0 containing decreasing concentrations of detergent (0.2% final) and filtered through a filter with a porosity of 0.45 µm, and then loaded onto a 1 ml Hi-Trap column (Pharmacia). These affinity chromatography supports chelate nickel atoms to which the histidine residues of the C-terminal end of the polypeptide attach. After washing, elution of the polypeptide is obtained with 50 mM formic acid buffer at pH 2.5.

Method 2: After elimination of the supernatant, the centrifugation pellet, composed essentially of inclusion bodies, is solubilized in one hour at room temperature by gentle stirring in the presence of 30 ml of 50 mM Tris-HCl buffer, pH 8.0, containing 8 M urea. After filtration through a filter with a porosity of 0.45 µm, the fraction is loaded onto a 1 ml Hi-Trap column (Pharmacia). After washing, the elution is carried out with 50 mM Tris-HCl buffer, pH 8.0,+8 M urea+500 mM imidazole. The eluted fraction is then dialyzed against 50 mM formic acid buffer at pH 2.5.

EXAMPLE 4

Preparation of the Polypeptide SEQ ID No. 30 According to the Invention

The polypeptide is expressed using the protocol described in example 3 and then purified according to the procedure described below.

The cell pellet, made up of the bacteria harvested from 500 ml of culture medium, is thawed and taken up in 100 ml of 50 mM Tris-HCl buffer at pH 8.0 in the presence of a protease inhibitor (Pefabloc, Interchim) at the concentration of 100 µM. Lysozyme is added at the concentration of 100 µg/ml and the mixture is incubated for 30 minutes at room temperature with stirring. The cells are then ruptured by sonication (4 cycles of two minutes) with an approximate power of 150 Watts. Benzonase (DNase, Merck) is then added along with 1 mM $MgCl_2$ and the mixture is incubated for 20 min at room temperature with stirring. After centrifugation (20 min at 10 000 g), the polypeptide according to the invention is mainly in the soluble fraction. After filtration through a filter with a porosity of 0.45 µm, the fraction is loaded onto a 1 ml Hi-Trap column (Pharmacia). After washing, the elution is carried out with 50 mM Tris-HCl buffer, pH 8.0,+500 mM imidazole. The eluted fraction is then dialyzed against 50 mM Tris-HCl buffer, pH 8.0.

The polypeptide, at a concentration of 0.4 mg/ml, is then placed in a 50 mM sodium formate buffer at pH 2.5. A TFE/polypeptide mixture is prepared by adding one volume of TFE per volume of polypeptide solution. The mixture thus obtained is incubated at room temperature for 15 min. 6 mg of Al phosphate are added, along with 50 mM sodium formate buffer so as to obtain a final volume of 0.5 ml.

The mixture is then incubated at 4° C. with stirring for a period of time which may vary between 15 min and 3 hours, so as to allow total adsorption of the protein onto the aluminum phosphate. After the adsorption step, the mixture is centrifuged for 5 minutes at approximately 10 000 g. The supernatant is eliminated and the pellet is resuspended in the initial volume by adding the required amount of PBS buffer. A second centrifugation followed by taking the pellet up in the same buffer makes it possible to eliminate the last traces of formic acid and TFE.

The preparation thus obtained forms the pharmaceutical composition which can be administered.

EXAMPLE 5

DSC Analysis of the Polypeptides According to the Invention

The analyses were carried out on a VP microcalorimeter (Microcal, Northampton, Mass., USA) in the following way:

Preparation of the Samples

Polypeptide concentration: 0.4–0.7 mg/ml, determined by the MicroBCA method (Pierce, Rockford, Ill., USA). The polypeptide is filtered before analysis (cutoff threshold of 0.22 µm), degassed for 8 min. in the Thermovac (Microcal, Northampton, Mass., USA) and then thermostatted at 24° C. The samples are in 50 mM Na formate buffer, pH 2.5.

Recording

After heating the apparatus, which consists of 6–10 thermocycles of the buffer against buffer, the polypeptide is placed in the measuring cell when the temperature of the cell is 25° C.

The thermocycle parameters are as follows: (1) equilibration for 15 min at 5° C.; (2) increase in the temperature from 5° C.–130° C. with a rate of 85° C./h; (3) equilibration for 3 min at 130° C. and (4) cooling from 130° C. to 5° C. (maximum rate) comprising the step of loading the following sample, at the temperature of 25° C., for the following measurement.

The analysis was carried out on the ectodomain of gp41 LAI, consisting of amino acids AA25-AA157, and on the polypeptides SEQ ID No. 31 and SEQ ID No. 30 according to the invention.

The protein concentration was 0.51 mg/ml for the whole ectodomain of gp41 and 0.63 mg/ml for the polypeptides according to the invention.

Figure 1:
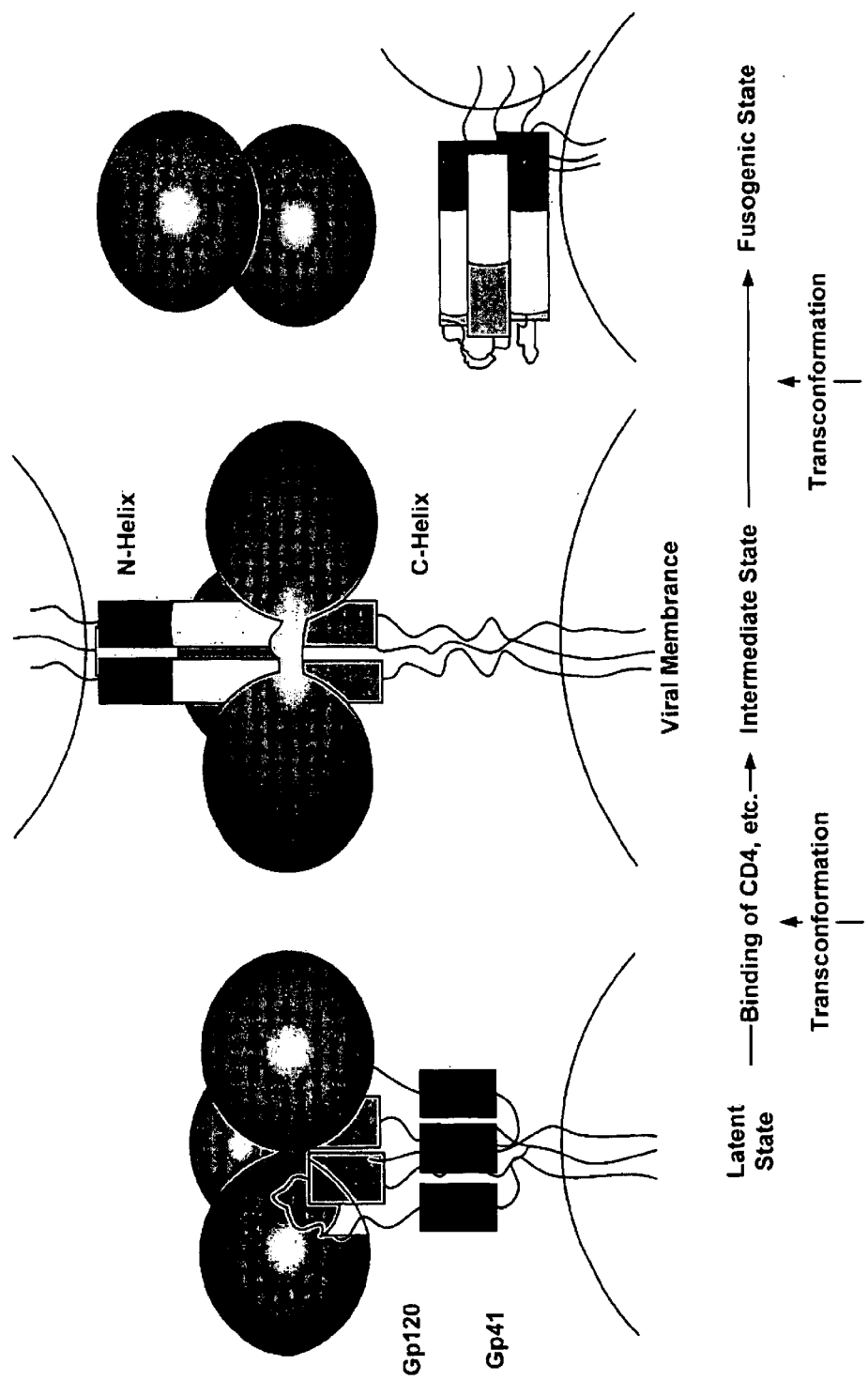
FIG. 1 is a diagrammatic representation of the phenomenon of conformational change of gp41 which precedes cell and viral membrane fusion.
Figure 2:
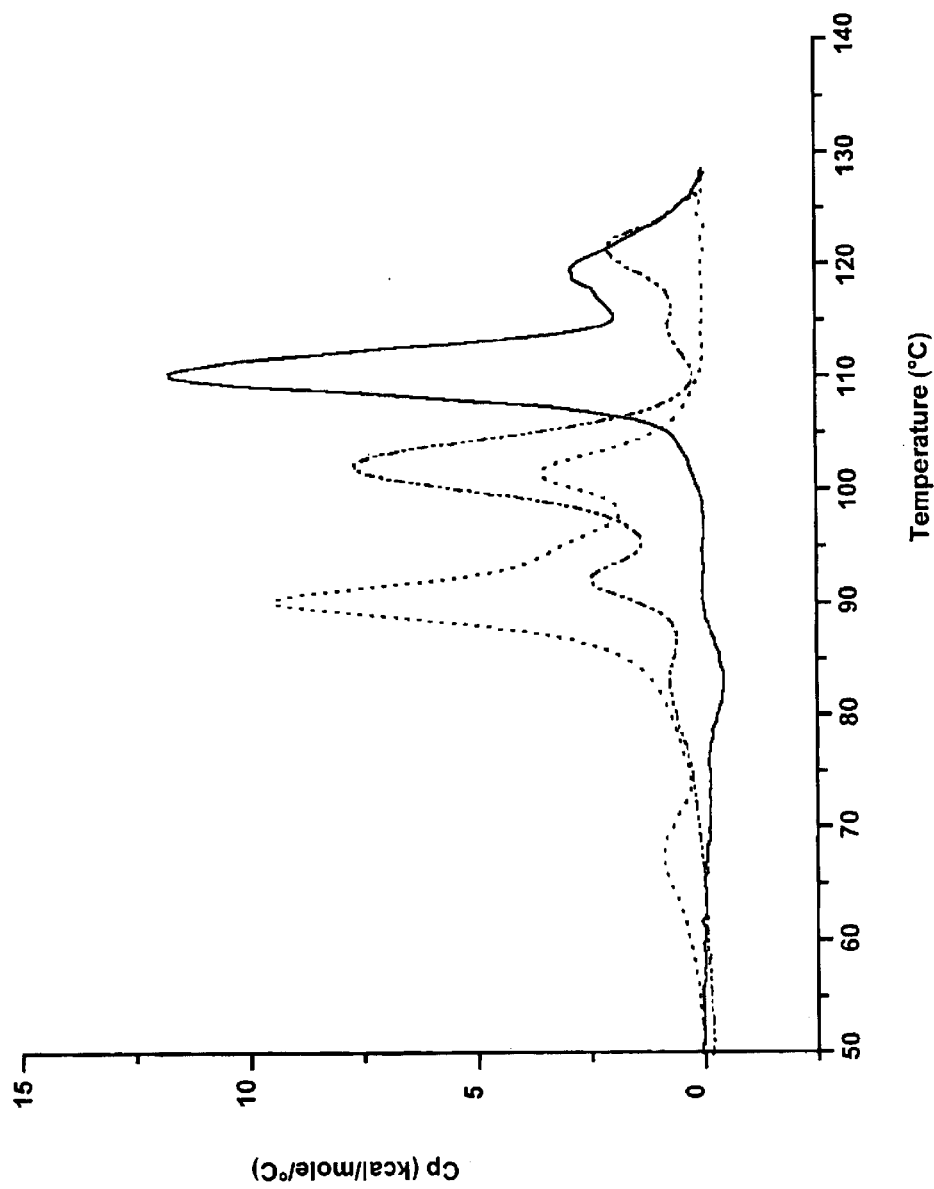
FIG. 2 represents a spectrum obtained using the DSC technique.

The results represented in FIG. 2 are given in table 2 below:

TABLE 2

| Sample | Tm (° C.) [standard deviation 0.2° C.] | ΔH (Kcal/mol) | $ΔH_{VH}$ (Kcal/mol) |
|---|---|---|---|
| Whole ectodomain of gp41 ☐ | 110.4 | 61 | 228 |
| Polypeptide SEQ ID No. 31 (-..-..-..) | 101.9 | 58 | 140 |
| Polypeptide SEQ ID No. 30 (.....) | 90.3 | 59 | 152 |

EXAMPLE 6

Circular Dichroism Analysis of the Polypeptides According to the Invention

The analyses were carried out on a spectropolarimeter (Jasco, Tokyo, Japan) under the following conditions: temp: 25° C.; cuvette: optical pathlength: 0.1 mm; polypeptide concentration: 1–2 mg/ml. The polypeptide is placed in the cuvette and the spectrum is recorded at a scanning rate of 10 nm/min. The spectra obtained are analyzed using the Spectra Analysis software from Jasco. The spectrum of the buffer is used to correct the background noise.

The analysis was carried out on the whole ectodomain of gp41 LAI (i.e. AA25–157) and on the polypeptide SEQ ID No. 31 according to the invention.

Figure 3:
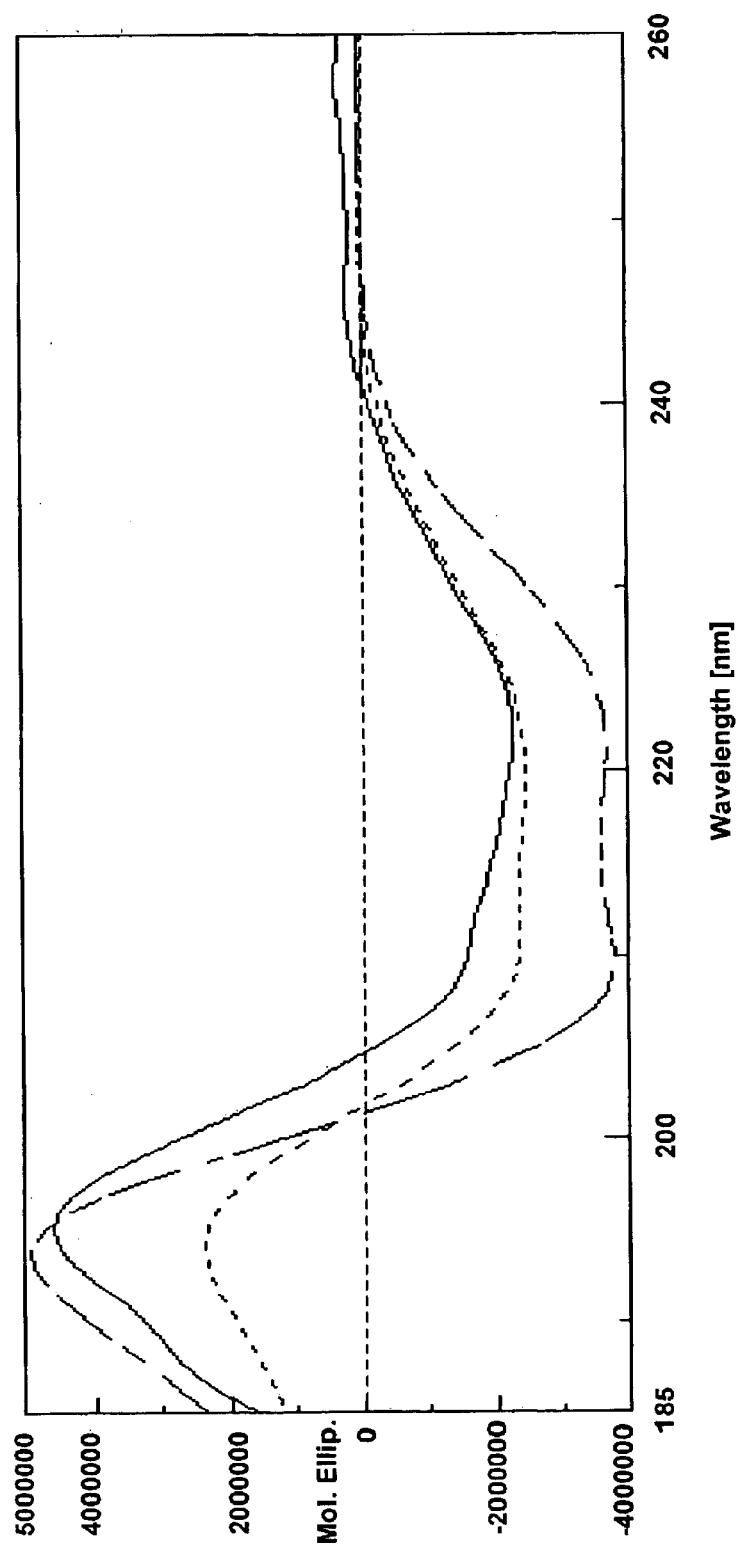
FIG. 3 represents a spectrum obtained using the circular dichroism technique.

The results represented in FIG. 3 show that the whole ectodomain has a degree of helicity of 69%, the polypeptide according to the invention has a degree of helicity of 70% and the polypeptide mixed with TFE has a degree of helicity of 100%.

EXAMPLE 7

Determination of the Humoral Immunity Induced by the Polypeptides of the Present Invention Polypeptides SEQ ID No.28, 29, 31 and 32 were tested in guinea pigs, in rabbits and in Cynomolgus monkeys according to the protocols described below.

Guinea pigs: Groups of 5 guinea pigs were injected 3 times, at 3-week intervals, in the thighs (biceps femoris muscle) with 20 µg per dose of antigen. Upon each injection, the animals received 0.5 ml of the formulation (0.25 ml in each thigh).

Serum samples were taken from the animals in order to analyze the antibodies before immunization, and 3 and 2 weeks after the $2^{nd}$ and $3^{rd}$ immunizations, respectively.

The two compositions tested: antigen+alum (aluminum phosphate, 6 mg per dose); and antigen+alum (aluminium phosphate, 6 mg per dose)+TFE were prepared in the following way:

a) For the formulations adjuvanted with aluminum phosphate: the antigen is in 50 mM formate medium, pH 2.5. The formulations are obtained by adding the alum to the antigen composition and incubating with gentle agitation for 30 minutes. The mixture is then centrifuged (5 minutes at 3 000 rpm), the supernatant being removed and replaced with PBS buffer so as to obtain a final concentration of 500 µl/dose. Resuspension is carried out using an ultrasound bath.

b) For the formulation: antigen+alum+TFE=1 vol. of TFE is added to one vol. of the antigen solution (formate 50 mM, pH 2.5) to obtain a final percentage of TFE of 50% vol. The mixture is incubated about 15 min. at RT and 6 mg of aluminium phosphate as well as some formate buffer were added to ajust the volume to 0.5 ml. The mixture thus obtained is incubated at 4° C. under agitation for about 15 min. to about 3 hrs. to allow adsorption of the antigen on the aluminium phosphate. The mixture is than centrifuged (5 min. at about 10.000 rpm). Resuspension of the pellet is carried out using PBS buffer (0.5 ml) and ultrasound bath. This last step can be carried out twice in order to remove all the TFE.

Rabbits: Groups of 2 rabbits were injected 3 times, at 3-week intervals, in the thighs with 40 µg per dose of antigen. Upon each injection, the animals received 1 ml of the formulation.

Serum samples were taken from the animals in order to analyze the antibodies before immunization, and then 3 and 2 weeks after the $2^{nd}$ and $3^{rd}$ immunizations, respectively.

The composition tested here: antigen+alum (aluminum phosphate, 6 mg per dose) was prepared in the following way: aluminum phosphate is added to the antigen in 50 mM formate medium, pH 2.5, the entire mixture being incubated for 30 minutes at +4° C. with gentle agitation (turning wheel). The tubes containing these preparations are then centrifuged (5 minutes at 3 000 rpm), the supernatant being removed and replaced with PBS buffer so as to obtain a final concentration of 1 ml/dose. Resuspension is carried out using an ultrasound bath.

Rhesus monkeys (macaca fascicularis): Groups of 2 monkeys were injected 3 times, at 1-month intervals, in the thighs (rectus femoris muscle) with 100 µg per dose of antigen adsorbed onto 6 ml of alum (aluminum phosphate). Upon each injection, the animals received 1 ml of the formulation.

Serum samples were taken from the animals in order to analyze the antibodies before immunization, and then 4 and 2 weeks after the $2^{nd}$ and $3^{rd}$ immunizations, respectively.

The composition tested here: antigen+alum was prepared using the protocol used for the rabbit experiment.

The results are given in the tables below:

As shown in table 1, the polypeptides of the invention induce significant, homogeneous and specific ELISA antibody levels against the gp41 ectodomain (produced in *E. coli* in a trimeric fusogenic form) and gp160 MN/LAI-2 (hybrid glycoprotein in which the gp120 subunit derives from the HIV-1 MN isolate and the gp41 subunit derives from the HIV-1 LAI isolate). These IgG responses virtually reach a plateau as soon as the $2^{nd}$ injection (table 1). The formulation in alginate appears to be 10 times less effective, in terms of specific antibody levels induced, than the formulation in alum.

TABLE 1

Guinea pig test - Antibody responses by ELISA

| | Anti-SEQ ID ectodomain gp41 IgG | | Anti-gp160 MN/LAI-2 IgG | |
|---|---|---|---|---|
| Immunogen | Post-2* IgG titers ($\log_{10}$) (number of positives) | Post-3* IgG titers ($\log_{10}$) (number of positives) | Post-2* IgG titers ($\log_{10}$) (number of positives) | Post-3* IgG titers ($\log_{10}$) (number of positives) |
| SEQ ID N° 28 (alum) | 5.1 ± 0.2 (5 +/ 5) | 5.1 ± 0.2 (5 +/ 5) | 4.7 ± 0.4 (5 +/ 5) | 5.0 ± 0.4 (5 +/ 5) |
| SEQ ID N° 28 alum + TFE | 5.4 ± 0.1 (5 +/ 5) | 5.3 ± 0.2 (5 +/ 5) | 4.7 ± 0.2 (5 +/ 5) | 5.0 ± 0.2 (5 +/ 5) |
| SEQ ID N° 31 alum | 5.1 ± 0.2 (5 +/ 5) | 5.2 ± 0.2 (5 +/ 5) | 5.0 ± 0.1 (5 +/ 5) | 5.3 ± 0.2 (5 +/ 5) |
| SEQ ID N° 31 alum + TFE | 5.2 ± 0.1 (4 +/ 4) | 5.1 ± 0.1 (4 +/ 4) | 4.7 ± 0.3 (4 +/ 4) | 4.9 ± 0.1 (4 +/ 4) |
| SEQ ID N° 32 alum | 5.0 ± 0.1 (5 +/ 5) | NT | 4.5 ± 0.3 (5 +/ 5) | NT |

*Geometric mean ± standard deviation ($\log_{10}$)
NB: All the preimmune sera tested are below the detection threshold (i.e. 1.9 $\log_{10}$ for the anti-gp 160 ELISA and 1.0 $\log_{10}$ for the anti-ectodomain gp41 ELISA).

The neutralizing activity of the post-$3^{rd}$ immunization sera was then evaluated initially with respect to the HIV-1 MN laboratory strain, on individual sera (at the DC Montefiori laboratory). As shown by the results obtained, no neutralization of the MN strain was observed. (table 2)

The neutralizing activity of the post-3 sera was also evaluated with respect to primary HIV-1 strains (laboratories of C. Moog and of D. Montefiori) (table 2). The analysis was carried out on individual sera. Advantageously, contrary to that which was observed for the MN strain, the guinea pigs showed significant neutralizing activities against several of the viral strains tested.

TABLE 2

Guinea pig test - Anti-HIV-1 neutralizing antibody responses

| | Laboratory strain | Primary isolates | | | | | |
|---|---|---|---|---|---|---|---|
| Immunogen | MN§ | Bal§ | SF162§ | 5768§ | Pavo§ | Bx08€ | Bx17€ |
| SEQ ID N° 31 (alum) | <0.55 | 97% | 88% | 97% | 95% | 4 | NT |
| SEQ ID N° 31 (alum) + TFE | <0.55 | 93% | NT | 88% | 86% | 4 | 4 |

TABLE 2-continued

Guinea pig test - Anti-HIV-1 neutralizing antibody responses

| Immunogen | Laboratory strain | Primary isolates | | | | | |
|---|---|---|---|---|---|---|---|
| | MN§ | Bal§ | SF162§ | 5768§ | Pavo§ | Bx08€ | Bx17€ |
| SEQ ID N° 28 (alum) | <0.55 | 93% | NT | 92% | NT | 10 | 10 |

§Lab. D. Montefiori: Results given for the post-3 sera (arithmetic value or %)
€Lab. C. Moog: Results given for the post-3 sera (arithmetic value)
NT: Not tested
NB: All the preimmune sera tested are below the positivity threshold (i.e., depending on the methods: <20 for the HIV-1 MN strain and <80% or <4 for the primary isolates).

TABLE 3

Rabbit test - ELISA antibody responses

IgG anti-ectodomain gp41

| Immunogen | Post-2* IgG titers ($\log_{10}$) (number of positives) | Post-3* IgG titers ($\log_{10}$) (number of positives) |
|---|---|---|
| SEQ ID N° 28 (alum) | 4.6 ± 0.2 (2 +/ 2) | 4.8 ± 0.2 (2+/ 2) |
| SEQ ID N° 31 (alum) | 4.5 ± 0.2 (2 +/ 2) | 4.8 ± 0.2 (2 +/ 2) |

TABLE 4

Monkey test - ELISA antibody responses

IgG Anti-ectodomain gp41

| Immunogen | Post-2* IgG titers ($\log_{10}$) (number of positives) | Post-3* IgG titers ($\log_{10}$) (number of positives) |
|---|---|---|
| SEQ ID N° 29 (alum) | 5.1 ± 0.0 (2 +/ 2) | 5.4 ± 0.0 (2 +/ 2) |
| SEQ ID N° 28 (alum) | 4.7 ± 0.2 (2 +/ 2) | 5.2 ± 0.2 (2 +/ 2) |
| SEQ ID N° 31 (alum) | 4.9 ± 0.7 (2 +/ 2) | 5.4 ± 0.3 (2 +/ 2) |
| SEQ ID N° 32 (alum) | 5.0 ± 0.1 (2 +/ 2) | 5.2 ± 0.2 (2 +/ 2) |

NB: The preimmune sera tested prove to be below the positivity threshold (1.0 $\log_{10}$).

The results given above clearly show that the polypeptides according to the invention are capable of inducing significant specific ELISA antibody levels in all the animal species tested. These IgG responses increased slightly between the 2$^{nd}$ and 3$^{rd}$ injection.

These antibodies, which have the property of neutralizing primary isolates, make the polypeptides according to the invention valuable candidates for immunization in humans.

What is claimed is:

1. A polypeptide comprising a sequence of formula I:

[N-S1]n-C-[S2-N]m wherein
N represents the sequence of amino acids 30 to 77 of gp41,
C represents the sequence of amino acids 117 to 154 of gp41,
S1 and S2 are, independently of one another, either absent or represent an amino acid sequence such that the sequence of formula I adopts an alpha-helical conformation as determined by the SOPMA program under the following conditions:
 a) number of conformational states=4
 b) similarity limit=8, and
 c) window width=70
and
 n=0 or 1; m=0 or 1 and m+n=1 or 2.

2. The polypeptide according to claim 1, wherein S1 is absent or represents the amino acid sequence D, DQ, DQQ, DQQL or DNNMT, and S2 is absent or represents the amino acid sequence W, WA, WAS, WASL or WASLW.

3. The polypeptide according to claim 1, wherein m+n=1.

4. The polypeptide according to claim 1, wherein N represents SEQ ID No. 26 and C represents SEQ ID No. 27.

5. The polypeptide according to claim 1 comprising an additional sequence of formula (G)a-S-(H)b wherein
G represents a glycine residue,
H represents a histidine residue,
a is greater than or equal to 4, and
b is greater than or equal to 6,
said sequence being linked via an amide bond to the NH$_2$- or COOH-terminal end of the polypeptide.

6. A conjugate comprising a polypeptide according to claim 1 conjugated to a carrier protein or peptide.

7. A DNA sequence encoding a polypeptide according to claim 1.

8. A DNA sequence encoding a polypeptide according to claim 6.

9. An expression vector comprising the DNA sequence according to claim 7.

10. An expression vector comprising the DNA sequence according to claim 8.

11. A host cell containing the vector according to claim 9.

12. A host cell containing the vector according to claim 10.

13. A method of preparing a polypeptide comprising the expression of said polypeptide using a host cell according to claim 11.

14. A method of preparing a polypeptide comprising the expression of said polypeptide using a host cell according to claim 12.

15. A composition comprising at least one polypeptide according to claim 1, a pharmaceutically acceptable excipient and, optionally, an adjuvant.

16. A composition comprising at least one conjugate according to claim 6, a pharmaceutically acceptable excipient and, optionally, an adjuvant.

17. A composition comprising at least one expression vector according to claim 9, a pharmaceutically acceptable excipient and, optionally, an adjuvant.

18. A composition comprising at least one expression vector according to claim 10, a pharmaceutically acceptable excipient and, optionally, an adjuvant.

19. The composition according to claim 15, wherein the composition is adapted for oral administration.

20. The composition according to claim 16 wherein the composition is adapted for oral administration.

21. The composition according to claim 17 wherein the composition is adapted for oral administration.

22. The composition according to claim 18 wherein the composition is adapted for oral administration.

23. The composition according to any one of claims 15 to 22 further comprising a pharmaceutically acceptable support.

24. A method of inducing an immune responce in a human, the method comprising administering an amount of a polypeptide according to claim 1 effective to induce the immune response in the human therefor.

25. A polypeptide consisting essentially of SEQ. ID. NO.: 28.

26. A polypeptide consisting essentially of SEQ. ID. NO.: 31.

27. A composition comprising the polypeptide according to claim 25, a pharmaceutically acceptable excipient and, optionally, an adjuvant.

28. A composition comprising the polypeptide according to claim 26, a pharmaceutically acceptable excipient and, optionally, an adjuvant.

29. The composition according to claim 27 or 28 further comprising a pharmaceutically acceptable support.

30. A method of inducing an immune response in a human, the method comprising administering an amount of a polypeptide according to claim 27 or 28 effective to induce the immune response in the human therefor.

* * * * *